(12) United States Patent
Johansson et al.

(10) Patent No.: US 9,522,170 B2
(45) Date of Patent: Dec. 20, 2016

(54) METHODS OF SCREENING COMPOUNDS FOR THE FIBRIL FORMATION OF Aβ PEPTIDES BASED ON A DECREASED TRIMER/MONOMER RATIO OF A CHAPERONE PROTEIN

(75) Inventors: Jan Johansson, Stockholm (SE); Jenny Presto, Uppsala (SE)

(73) Assignee: ALPHABETA AB, Djursholm (SE)

( * ) Notice: Subject to any disclaimer, the term of this patent is extended or adjusted under 35 U.S.C. 154(b) by 0 days.

(21) Appl. No.: 14/009,360

(22) PCT Filed: Mar. 30, 2012

(86) PCT No.: PCT/SE2012/050352
§ 371 (c)(1),
(2), (4) Date: Oct. 17, 2013

(87) PCT Pub. No.: WO2012/138284
PCT Pub. Date: Oct. 11, 2012

(65) Prior Publication Data
US 2014/0030274 A1    Jan. 30, 2014

(30) Foreign Application Priority Data
Apr. 5, 2011    (SE) ...................................... 1150299

(51) Int. Cl.
| | |
|---|---|
| *G01N 33/53* | (2006.01) |
| *G01N 33/567* | (2006.01) |
| *A61K 38/00* | (2006.01) |
| *A61K 49/00* | (2006.01) |
| *A61K 38/17* | (2006.01) |
| *G01N 33/68* | (2006.01) |
| *C07K 14/47* | (2006.01) |
| *G01N 33/50* | (2006.01) |

(52) U.S. Cl.
CPC ........... *A61K 38/1709* (2013.01); *C07K 14/47* (2013.01); *G01N 33/5058* (2013.01); *G01N 33/6896* (2013.01); *A61K 38/00* (2013.01); *G01N 2500/02* (2013.01); *G01N 2800/12* (2013.01); *G01N 2800/2821* (2013.01)

(58) Field of Classification Search
CPC ................ G01N 33/6896; G01N 33/68; G01N 2333/4709; G01N 2800/2821; G01N 2800/52; G01N 2800/2814; G01N 2500/02; C40B 30/04; C07K 14/4711
See application file for complete search history.

(56) References Cited

U.S. PATENT DOCUMENTS

| 8,211,442 B2 | 7/2012 | Kido et al. .................. 424/204.1 |
| 8,268,321 B2 | 9/2012 | Kido et al. .................. 424/184.1 |
| 8,785,390 B2 | 7/2014 | Johansson | |
| 2002/0119463 A1 | 8/2002 | Faris et al. | |
| 2003/0224982 A1 | 12/2003 | Li et al. .......................... 514/12 |
| 2004/0235813 A1 | 11/2004 | Wanker et al. | |
| 2005/0070477 A1 | 3/2005 | Cochrane | |
| 2007/0141073 A1 | 6/2007 | Kido et al. .................. 424/185.1 |
| 2009/0130131 A1 | 5/2009 | Kido et al. .................. 424/185.1 |
| 2012/0122794 A1 | 5/2012 | Johansson .................... 514/17.8 |
| 2012/0178119 A1 | 7/2012 | Miyawaki et al. | |
| 2013/0172262 A1 | 7/2013 | Johansson .................... 514/17.8 |

FOREIGN PATENT DOCUMENTS

| JP | 2002-528555 A | 9/2002 | |
| JP | 2007-132849 A | 5/2007 | |
| WO | WO 88/03170 | 5/1988 | ............. C12P 21/00 |
| WO | WO-00/26251 A2 | 5/2000 | |
| WO | WO0071671 | * 11/2000 | |
| WO | WO 02/041002 | 5/2002 | ............. G01N 33/68 |
| WO | WO 03/090682 | 11/2003 | |
| WO | WO 2004/056310 | 7/2004 | |
| WO | WO2005023833 | * 3/2005 | |
| WO | WO2005023858 | * 3/2005 | ............. C07K 14/47 |
| WO | WO2005047484 | * 5/2005 | |
| WO | WO 2005/055994 | 6/2005 | ............. A61K 31/00 |
| WO | WO 2005/097182 | 10/2005 | ............. A61K 39/39 |
| WO | WO 2006/138355 | 12/2006 | ............. A61K 38/17 |
| WO | WO2006138355 | * 12/2006 | |
| WO | WO 2007/005672 | 1/2007 | |
| WO | WO 2007/018152 | 2/2007 | ............. A61P 37/08 |
| WO | WO 2008/066734 | 6/2008 | ........... A01K 67/027 |
| WO | WO2008066734 | * 6/2008 | |
| WO | WO 2008/151235 | 12/2008 | |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Hedlund et al. BMC Research Notes; 2009: 2: 180.*
International Preliminary Report on Patentability dated Oct. 8, 2013 for International Appl. No. PCT/SE2012/050352.
U.S. Appl. No. 14/279,589, filed May 16, 2014.
U.S. Appl. No. 14/287,742, filed May 27, 2014.
Office Action dated Oct. 10, 2013 issued in U.S. Appl. No. 13/805,574.
Office Action dated Feb. 24, 2015 issued in U.S. Appl. No. 14/287,742.
Office Action dated Oct. 31, 2014 issued in U.S. Appl. No. 14/287,742.
Office Action dated Jul. 13, 2015 issued in U.S. Appl. No. 14/279,589.
Office Action dated Jan. 20, 2016 issued in U.S. Appl. No. 14/279,589.

(Continued)

*Primary Examiner* — Chang-Yu Wang
(74) *Attorney, Agent, or Firm* — Harness, Dickey & Pierce, P.L.C.

(57) ABSTRACT

A method involves screening a candidate compound for activity in the treatment of a condition associated with formation of amyloid protein fibrils in a mammal, such as Alzheimer's disease. It is determined whether the trimer/monomer ratio of a chaperone protein is decreased in the presence of the candidate compound. The chaperone protein is or has a high identity to the Brichos domains of Bri2, Bri3 or proSP-C from human. Monomers of the chaperone proteins and/or compounds that promote formation of these monomers are useful for medical treatment of the condition.

5 Claims, 12 Drawing Sheets

(56) References Cited

FOREIGN PATENT DOCUMENTS

| WO | WO 2009/009396 | 1/2009 | ............ C07K 14/47 |
| --- | --- | --- | --- |
| WO | WO 2010/087771 | 8/2010 | ............ A61K 38/17 |
| WO | WO-2011/019082 A1 | 2/2011 | |
| WO | WO2011162655 | * 12/2011 | |

OTHER PUBLICATIONS

Accession No. Q3T0P7, Jan. 24, 2006 [online] [retrieved on Jan. 26, 2011] Retrieved from EBI; Database UniProt,<URL: http://srs.ebi.ac.uk/srsbin/cgi-bin/wgetz?-e+[uniprotid:ITM2B_BOVIN]I[uniprot-acc:ITM2B_BOVIN]+-noSession>.

Accession No. Q52N47, Jul. 24, 2007 [online] [retrieved on Jan. 26, 2011] Retrieved from EBI; Database UniProt, <URL: http://srs.ebi.ac.uk/srsbin/cgi-bin/wgetz?-e+[uniprotid:ITM2B_PIG]I[uniprot-acc:ITM2B_PIG]+-noSession>; whole document; abstract.

Accession No. O89051, Jul. 15, 1999 [online] [retrieved on Jan. 26, 2011] Retrieved from EBI; Database UniProt, <URL: http://srs.ebi.ac.uk/srsbin/cgi-bin/wgetz?-e+[uniprotid: ITM2B_MOUSE]I[uniprot-acc:ITM2B_MOUSE]+noSession>; whole document; abstract.

Accession No. Q5XIE8, Jan. 24, 2006[online] [retrieved on Jan. 26, 2011] Retrieved from EBI; Database UniProt, <URL:http://srs.ebi.ac.uk/srsbin/cgi-bin/wgetz?-e+[uniprotid: ITM2B_RAT]I[uniprot-acc:ITM2B_RAT]+-noSession>; whole document abstract.

Casals, C., et al. (2008), C-terminal, endoplasmic reticulum-lumenal domain of prosurfactant protein C—structural features and membrane interactions, *The FEBS Journal*, 1-12.

Chaudhuri, T., et al. (2006), "Protein-misfolding diseases and chaperone-based therapeutic approaches", *The FEBS Journal*, 273: 1331-1349.

Citron, M. (2010), "Alzheimer's disease: strategies for disease modification", *Nature Reviews*, 9: 387-398.

DebBurman, S., et al. (1997), "Chaperone-supervised conversion of prion protein to its protease-resistant form" *Proc. Natl. Acad Sci. USA*, 94:13938-13943.

Evans, C., et al. (2006), "Heat shock proteins 70 and 90 inhibit early stages of amyloid β-(1-42) aggregation in vitro" *The Journal of Biological Chemistry*, 281(44):33182-33191.

Fitzen, M., et al. (2009), "Peptide-binding specificity of the prosurfactant protein C brichos domain analyzed by electrospray ionization mass spectrometry", *Rapid Communication in Mass Spectrometry*, 23: 3591-3598.

Fotinopoulou, A., et al. (2005) "BRI2 Interacts with amyloid precursor protein (APP) and regulates amyloid β (Aβ) production" *The Journal of Biological Chemistry*, 280(35): 30768-30772.

Hellstrand, E., et al. (2010) "Amyloid β-protein aggregation produces highly reproducible kinetic data and occurs by a two-phase process" *ACS Chemical Neuroscience*, 1:13-18.

Johansson, J. (2003), "Molecular determinants for amyloid fibril formation: lessons from lung surfactant protein C", *Swiss Med Wkly*, 133: 275-282.

Johansson, J., et al. (2006), "The brichos domain-containing C-terminal part of pro-surfactant protein C binds to an unfolded polyval-transmembrane segment", *The Journal of Biological Chemistry*, 281(30): 21032-21039.

Johansson, H., et al. (2009), "Preventing amyloid formation by catching unfolded transmembrane segments", *J. Mol. Biol.*, 389: 227-229.

Kim, J., et al. (2008), "BRI2 (ITM2b) inhibits Aβ deposition In Vivo", *The Journal of neuroscience*, 28(23): 6030-6036.

Klucken, J., et al. (2004), "Hsp70 reduces α-synuclein aggregation and toxicity", *The Journal of Biological Chemistry*, 279(4): 25497-25502.

Martin, L., et al. (2008), "Regulated intramembrane proteolysis of Bri2 (Itm2b) by ADAM10 and SPPL2a/SPPL2b" *The Journal of Biological Chemistry*, 283 (3): 1644-1652.

Matsubara, E., et al. (1996), "Apolipoprotein J and alzheimer's amyloid β solubility" *Biochem J.*, 316:671-679.

Matsuda, S., et al. (2009), "Maturation of BRI2 generates a specific inhibitor that reduces APP processing at the plasma membrane and in endocytic vesicles" *Neurobiology of Aging*, 7384:1-9.

McHattie, S., et al. (1999), "Clusterin prevents aggregation of neuropeptide 106-126 in vitro" *Biochemical and Biophysical Research Communications*, 259:336-340.

Nerelius, C., et al. (2008), "Mutations Linked to interstitial lung disease can abrogate anti-amyloid function of prosurfactant protein C", *Biochem J.*, 416: 201-209.

Nerelius, C., et al. (2009), "Anti-amyloid activity of the C-terminal domain of proSP-C against amyloid β-peptide and medin", *Biochemistry*, 48: 3778-3786.

Nerelius, C., et al. (2010), "Amino Acid sequence determinants and molecular chaperones in amyloid fibril formation", *Biochemical and Biophysical Research Communications*, 396: 2-6.

Peng, S., et al. (2010), "The extracellular domain of Bri2 (ITM2B) binds the ABri peptide (1-23) and amyloid β-peptide (Aβ1-40): Implications for Bri2 effects on processing of amyloid precursor protein and Aβ aggregation" *Biochemical and Biophysical Research Communications*, 393:356-361.

Sánchez-Pulido, L., et al. (2002), "BRICHOS: a conserved domain in proteins associated with dementia, respiratory distress and cancer" *Trends in Biochemical Sciences*, 27(7):329-332.

Shimshek, D., et al. (2010), "The HSP70 molecular chaperone is not beneficial in a mouse model of Asynucleinopathy", *PLoS One*, 5(4): e10014.

Thompson, J., et al. (1994), "Clustal W: improving the sensitivity of progressive multiple sequence alignment through sequence weighting, position-specific gap penalties and weight matrix choice", Oxford University Press, 22(22): 4673-4680.

Tomidokoro, Y., et al. (2005) "Familial Danish dementia co-existence of Danish and Alzheimer amyloid subunits (ADan and Aβ) in the absence of compact plaques" *The Journal of Biological Chemistry*, 280(44):36883-36894.

Vickers, J., (2002), "A vaccine against alzheimer's disease", *Drugs Aging*, 19(7):487-494.

Westermark, P., (2005), "Aspects on human amyloid forms and their fibril polypeptides", *The FEBS Journal*, 5942-5949.

Office Action dated Oct. 15, 2012 issued in U.S. Appl. No. 13/145,096.

Office Action dated Feb. 27, 2013 issued in U.S. Appl. No. 13/145,096.

Office Action dated Jul. 31, 2013 issued in U.S. Appl. No. 13/805,574.

Office Action dated Aug. 29, 2013 issued in U.S. Appl. No. 13/145,096.

Extended European Search Report dated Jul. 17, 2009 issued in EP Application No. 09151790.4.

International Search Report and Written Opinion dated Mar 18, 2010 issued in PCT Application No. PCT/SE2010/050097.

International Preliminary Report on Patentability dated Sep. 15, 2010 issued in PCT Application No. PCT/SE2010/050097.

International Search Report and Written Opinion dated Feb. 3, 2011 issued in PCT Application No. PCT/SE2010/050723.

International Search Report dated Sep. 11, 2012 issued in PCT Application No. PCT/SE2012/050352.

International Preliminary Report on Patentability dated Dec. 28, 2012 issued in PCT Application No. PCT/SE2010/050723.

* cited by examiner

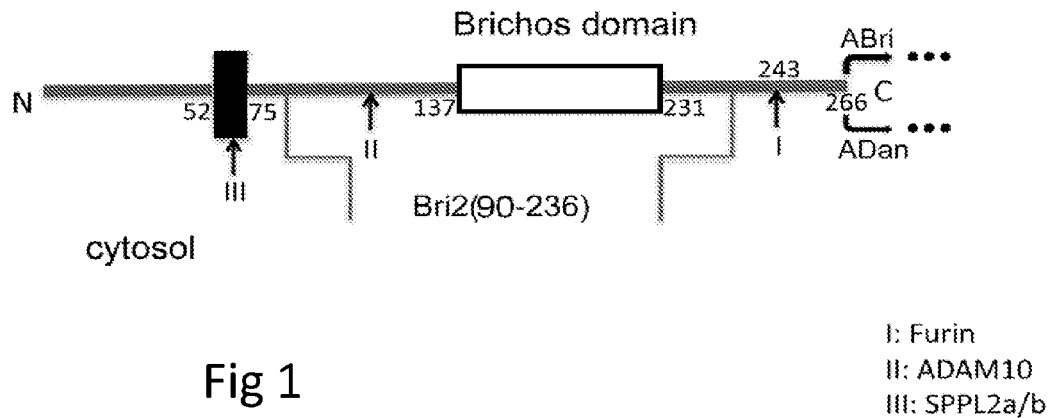

Fig 1

I: Furin
II: ADAM10
III: SPPL2a/b

```
Human   FADSDPANIVHDFNKKLTAYLDLNLDKCYVIPLNTSIVMPPRNLLELLIN
Chimp   FADSDPANIVHDFNKKLTAYLDLNLDKCYVIPLNTSIVMPPRNLLELLIN
Bovine  FADSDPANIVHDFNKKLTAYLDLNLDKCYVIPLNTSIVMPPKNLLELLIN
Pig     FADSDPANIVHDFNKKLTAYLDLNLDKCYVIPLNTSIVMPPRNLLELLIN
Mouse   FADSDPANIVHDFNKKLTAYLDLNLDKCYVIPLNTSIVMPPKNLLELLIN
Rat     FADSDPANIVHDFNKKLTAYLDLNLDKCYVIPLNTSIVMPPRNLLELLIN
Non-id                                           *

Human   IKAGTYLPQSYLIHEHMVITDRIENIDHLGFFIYRLCHDKETYKL
Chimp   IKAGTYLPQSYLIHEHMVITDRIENIDHLGFFIYRLCHDKETYKL
Bovine  IKAGTYLPQSYLIHEHMVITDRIENIDHLGFYIYRLCHDKETYKL
Pig     IKAGTYLPQSYLIHEHMVITDRIENIDHLGFYIYRLCHDKETYKL
Mouse   IKAGTYLPQSYLIHEHMVITDRIENVDNLGFFIYRLCHDKETYKL
Rat     IKAGTYLPQSYLIHEHMVITDRIENVDHLGFFIYRLCHDKETYKL
Non-id                          *       *
```

Fig 2

A proSP-C
H2N— [____] —COOH
        ↓
    H2N—[_]—COOH

CTproSP-C
    H2N—[____]—COOH

B

```
Bovine   HMSQKHTEMVLEMSIT-GPEAQORLIALSERVGTTATFSIGSTGTVVYDYQRLLIAYKPAPGTCCYIMKMAP
Human    HMSQKHTEMVLEMSIG-APEAQQRLIALSEHLVTTATFSIGSTGLVVTDYQQLLIAYKPAPGTCCYIMKTAP
Rhesus   HMSQKHTEMVLEMSIG-APEAQQHLIARSGHLVTTATFSFGSTGLVVYDYQRLLIAYKPAPGTWCYIMKTAP
Mouse    HMSQKHTEMVLEMSIG-APETQKRLAPSERADTIATFSIGSTGIVVYDYQRLLIAYKPAPGTYCYIMKMAP
Mink     HMSQKHTEMVLEMSIG-APETQKRLIAYKPAGTCCYIMKMAP (partial)
Rabbit   HMSQKHTEMVLEMSIG-APEVQQRLIAISEWAGTTATFPIGSTGIVTCDYQRLLIAYKPAPGTCCYIMKMAP
Rat      HMSQKHTEMVLEMSIGGAPETQKRLALSEHTDTIATFSIGSTGIVLYDYQRLLIAYKPAPGTYCYIMKMAP
Strict   HMSQKHTEMVLEMS---- ---T-ATF--GSTG-V--DYQ--LL-AYKPAPGT-CY-MR-AP Bovine   QNIPSLEALTRKLQMFQ------AKPQVPSSKKLGQEEGHDAGSAF---SG-DLAFLGRTVSTLCGEVPLYYT
Human    ESIPSLEALNRKVHNFQMECSIQAKPAVPTSKLGQAEGRDAGSAP---SGGDPAFLGMAVNTLGEVPLIYI
Rhesus   ESIPSLEALTRKVQNFQ------ANPAVPTSKLDQVEGRDAGSAP---SRGDLAFLGMAVSTLGGEVPLYI
Mouse    ESIPSLEAPARKLQMFR------AKPSTPTSKLGQEEGHDTGSESDSSGRDIAFLGLAVSTLCGELPLYYI
Mink     ENIPSLEALTRKFQNFQ------YRPAVSTSKLGQEVEGHNAGSA----SPGDLDFLGTTVSTLCGEVPLYYI
Rabbit   DSIPSLEALARKFQANP------AEPPTQR---GDKGPAAGPA---SSGGEAFLGAAVSTLCGEVPLIYI
Rat      ESIPSLEALARKFKMFQ------AKSSTPTSKLGQEEGHSAGSDSDSSGRDLAFLGLAVSTLCGELPLIYI
Strict   --IPSLEA--RK----------------------------------- ----S---G--FLG--PL-Y-
```

*Fig. 3*

```
proSP-C  LVTTATFSIGSTGLVVYDYQQLLIAYKPAPGTCCYIMKIAPESIPS-----LEALNRKVH
Bri2     SVPVPEFADSDPANIVHDFNKKLTAYLDLNDKCYVIPLNTSIVMPPRNLLELLINIKAG
          *  ::   ::***:::   :   * **      *  *::   ::    :*  * proSP-C  NFQMECSLQAKPAVPTSKLGQAEGRDAGSAPSGGDPAFLGMAVNTLCGEVPLYYI
Bri2     TYLPQSYLIHEHMVITDRIENIDH------------LGFFYRLCHDKETYKL
          : *:  **:*: *:*.:   : ::            **:*  * *: ** *:  ::
```

Fig 8

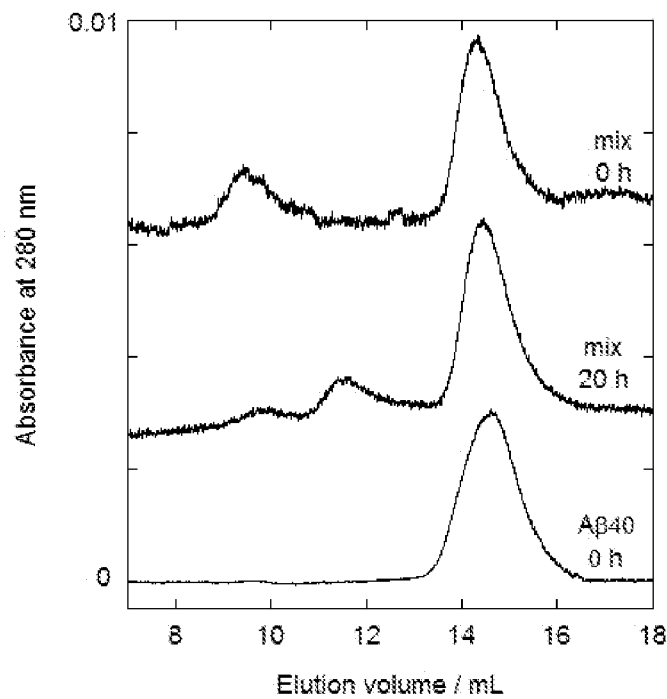
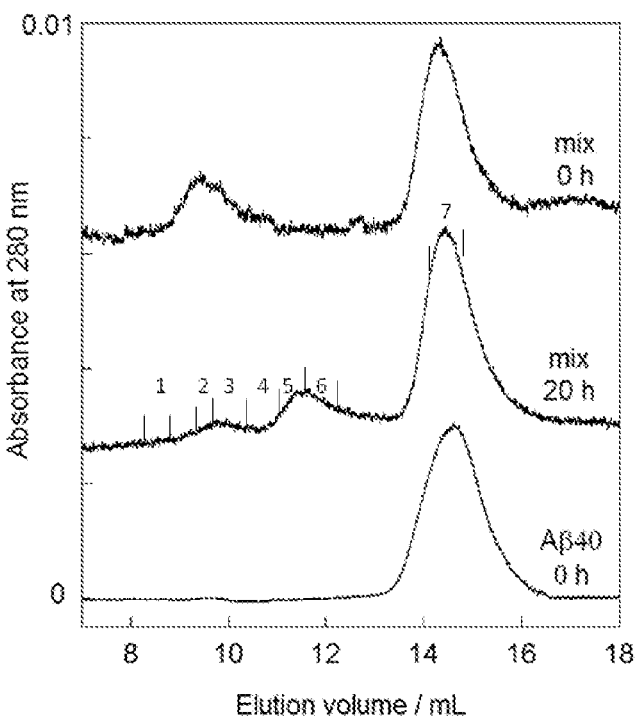
Fig 11

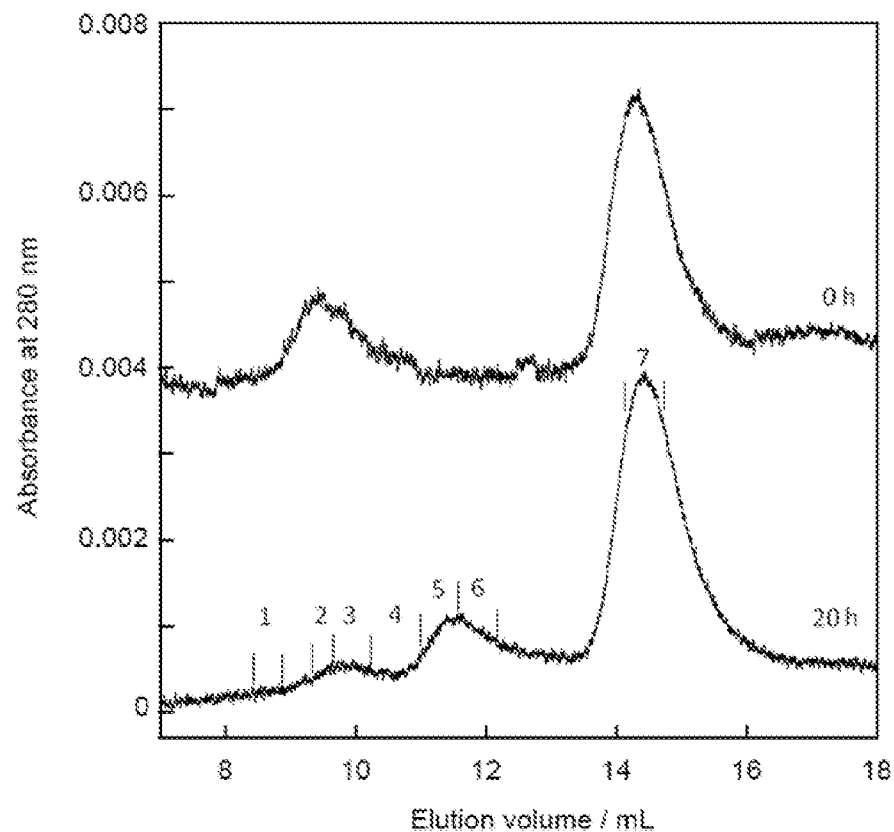
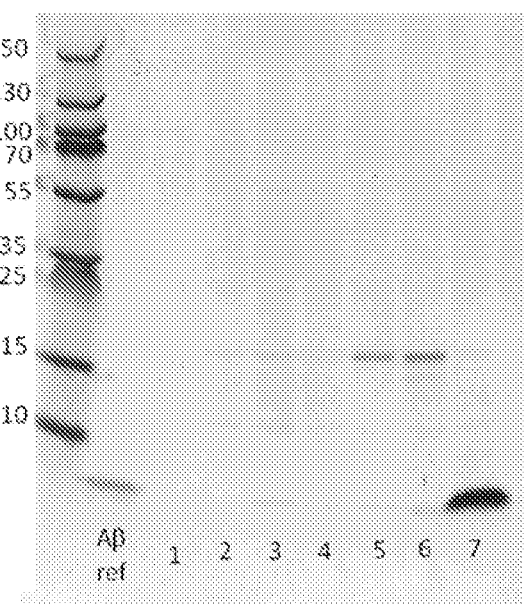
Fig 12A

US 9,522,170 B2

METHODS OF SCREENING COMPOUNDS FOR THE FIBRIL FORMATION OF Aβ PEPTIDES BASED ON A DECREASED TRIMER/MONOMER RATIO OF A CHAPERONE PROTEIN

PRIORITY STATEMENT

This application is a national stage application under 35 U.S.C. §371 of PCT International Application No. PCT/SE2012/050352 which has an International filing date of 30 Mar. 2012, and which claims priority under 35 U.S.C. §119 to Sweden Application No. 1150299-4 filed 5 Apr. 2011. The contents of each application recited above are incorporated herein by reference in their entirety.

REFERENCE TO A SEQUENCE LISTING

The material in the ASCII text file entitled "61351279_1.txt" is hereby incorporated by reference in its entirety. The ASCII text file entitled "61351279_1.txt" was created on 1 Oct. 2014 and the size is 14 KB.

FIELD OF THE INVENTION

The present invention pertains to the field of medicine. More specifically, this invention relates to medicaments for treatment and medical treatment of conditions associated with formation of amyloid protein fibrils in a mammal, such as man. The conditions include Alzheimer's disease, familial Danish dementia, familial British dementia and interstitial lung disease (ILD).

TECHNICAL BACKGROUND TO THE INVENTION

An increasing number of neurodegenerative conditions are linked to protein misfolding and aggregation, such as Alzheimer's disease, familial British or Danish dementia, and interstitial lung disease. These diseases are characterized by protein deposits, e.g. in the brain parenchyma and cerebral arteries, and occur in inherited and sporadic forms. Even though these diseases have different clinical symptoms, they share some common pathological features including formation of protein aggregates. From a biochemical point of view, the proteins involved have a tendency to form β-sheet structures and are prone to aggregate into amyloid fibrils. Alzheimer's disease and familial British or Danish dementia display several similar neuropathological hallmarks. Amyloid plaques, neurofibrillary tangles, Congophilic amyloid angiopathy and neurodegeneration are observed.

Alzheimer's disease is one of the most common causes of dementia in man. It is a chronic and fatal disease associated with neural cell degeneration in the brain of the affected individual, characterized by the presence of amyloid plaques consisting of extracellular deposits of amyloid β-peptide (Aβ-peptide). The neural cell atrophy caused by Aβ aggregation results in deficiency of acetylcholine and other signaling substances. It is known that Aβ-peptide, having 40-42 amino acid residues, is produced by processing of the amyloid precursor protein (APP, 695-770 amino acid residues), which is a type I membrane protein normally expressed by the neurons of the central nervous system, but the reasons for this processing are incompletely understood. The released Aβ peptide contains a part of the transmembrane region of APP (Aβ residues 29-40/42) and includes a discordant helix, i.e. a helix composed of amino acids with a high propensity to form β-strands. Aβ is prone to misfold and aggregate when removed from its stabilising membrane environment.

Bri2 (SEQ ID NO: 1, also referred to as integral membrane protein 2B, ITM2B), is a 266-residue type II membrane protein (FIG. 1) with ubiquitous expression, whose function and folded structure are unknown. Bri2 is proteolytically cleaved at three locations; cleavage by furin in the C-terminal region generates a 23-residue peptide (Bri23), processing of the ectodomain by ADAM10 results in release of the Brichos domain from the membrane-bound N-terminal part, and intramembrane cleavage by SPPL2a/2b liberates the intracellular domain. Familial British and Danish dementia are caused by mutations in the Bri2 gene that result in a loss of a stop codon, which in turn results in two different 11-residue extensions of the C-terminal part, and, after furin cleavage, generation of 34-residue peptides (ABri and ADan, respectively) instead of the normally released Bri23. The longer peptides are prone to aggregation into amyloid fibrils and deposition in brain tissue or cerebral vessels, with concomitant neuronal loss and dementia.

Recent studies have shown that Bri2, and/or fragments thereof, and Aβ co-localize in amyloid plaques in brain parenchyma and vessels, suggesting that the proteins interact at some stage during misfolding and aggregation. Using transfected cell lines, Bri2 has been found to interact with APP, and to modulate APP processing by increasing β-secretase generated fragments. Generation of a fusion protein containing Bri2 and Aβ40 indicates that the Bri protein can affect Aβ aggregation properties, and using a transgenic mouse model, Bri23 has been proposed to interact with Aβ42 and prevent its aggregation (Kim et al. J. Neurosci. 28: 6030-6036 (2008); WO 2009/009396). It has also been suggested that Aβ production can be reduced or prevented by a protein containing the first 102 amino acid residues of Bri2 (WO 2006/138355).

Current therapeutic approaches for treatment of Alzheimer's disease are mainly directed to treating the symptoms and include cholinergic replacement therapy, e.g. inhibition of acetylcholinesterase, small inhibitors that interact with soluble Aβ oligomers, and so-called β-sheet breakers that prevent elongation of already formed β-sheet structures Monoclonal antibodies against Aβ peptide prevent aggregation into neurotoxic fibrils and dissolve already formed amyloid. However, antibody therapy is very costly and associated with side-effects of varying seriousness. Vaccination with β-amyloid in transgenic mice models of Alzheimer's disease has shown a significant reduction in the number of amyloid plaques and overall amyloid burden and even some improvement in cognitive performance.

Another suggested strategy to prevent aggregation has been to utilize molecules that are functionally defined as chaperones. Chaperones play an important role by aiding the correct folding of proteins in the complex intracellular milieu. A number of molecular chaperones, such as heat-shock proteins (Hsp), are known to be important in the folding process and have been extensively studied. Some of these chaperones are apparently able to interact with and have an impact on the amyloid fibril formation of certain polypeptides. Aggregation of $A\beta_{1-42}$ is inhibited by Hsp90 or the combination Hsp70/Hsp40 (C G Evans et al, J Biol Chem 281: 33182-33191, 2006). Furthermore, the extracellular chaperone clusterin (apolipoprotein J) has been shown to inhibit fibril formation of a number of polypeptides including Aβ (E Matsubara et al, Biochem J 316(Pt 2): 671-679, 1996) and a fragment of the prion protein (S McHattie and N Edington, Biochem Biophys Res Commun 259: 336-340, 1999). The role of the structurally diverse chaperones in prevention of amyloid diseases is not established and some reports even indicate that protein chaperones promote amyloid fibril formation, see e.g. S K Deb-Burman et al, Proc Nat Acad Sci USA 94: 13938-13943, 1997. In addition to molecular chaperones, the effects of chemical and pharmacological chaperones have been studied in the context of misfolding diseases.

Nerelius et al., Biochemistry, 48: 3778-3786 (2009) and Johansson et al., J. Mol. Biol. 389(2): 227-229 (2009) show that surfactant protein C (SP-C) as well as Aβ-peptide amyloid fibril formation can be prevented by CTproSP-C, i.e. the C-terminal fragment of the SP-C precursor proSP-C. It is suggested that Aβ-peptide binds to CTproSP-C trimers to pentamers. Casals et al., FEBS Journal, 275: 536-547 (2008) demonstrates that the CTproSP-C predominantly exists as a trimer in the absence of the remaining parts of proSP-C, although several other oligomerization states are observed, including oligomers of trimers.

Peng et al., Biochem. Biophys. Res. Commun., 393: 356-361 (2010) show that the extracellular domain of Bri2 (also referred to as integral membrane protein 2B, ITM2B) binds to Aβ-peptide and prevents Aβ-peptide amyloid fibril formation.

Despite these advances in the art, there is a strong need of improved and alternative therapies for treatment of conditions associated with formation of amyloid protein fibrils in a mammal, such as man.

SUMMARY OF THE INVENTION

It is an object of the invention to decrease the tendency of proteins that are prone to fibrillate to aggregate into amyloid fibrils, or even prevent proteins that are prone to fibrillate from aggregating into amyloid fibrils.

It is also an object of the invention to decrease formation of amyloid plaques consisting of extracellular deposits in the brain of a mammal of proteins that are prone to fibrillate.

It is another object of the invention to provide a new treatment option for conditions associated with formation of amyloid protein fibrils in a mammal, including man.

It is also an object of the invention to provide a new treatment option for the treatment of Alzheimer's disease, familial Danish and British dementia, and interstitial lung disease in a mammal, including man.

It is a further object of the invention to provide a new target that is involved in conditions associated with formation of amyloid protein fibrils, which target is useful for identifying compounds that are active in the treatment of these conditions It is yet another object of the invention to provide compounds, combinations of compounds and pharmaceutical compositions comprising such compounds for the treatment of conditions associated with formation of amyloid protein fibrils.

It is an object of the present invention to provide a method of treating a condition associated with formation of amyloid protein fibrils, involving interaction with the new target.

The present invention is generally based on the insight that monomers of chaperone proteins which have a high identity to the Brichos domains of Bri2, Bri3 or proSP-C from human and/or compounds that promote formation of these monomers are useful for medical treatment of these conditions.

Thus, for these and other objects that will be evident from the following description, the present invention provides according to a first aspect a method of screening one or more candidate compound(s) for activity in the treatment of a condition associated with formation of amyloid protein fibrils in a mammal, comprising determining whether the trimer/monomer ratio of a chaperone protein is decreased in the presence of said one or more candidate compound(s). The chaperone protein is comprising more than or equal to 80 amino acid residues and is comprising an amino acid sequence having at least 70% identity to an amino acid sequence selected from the group consisting of residues 90-243 of Bri2 from human (SEQ ID NO: 2), the Brichos domain of Bri2 from human (SEQ ID NO: 3), residues 97-242 of Bri3 from human (SEQ ID NO: 4), the Brichos domain of Bri3 from human (SEQ ID NO: 5), CTproSP-C from human (SEQ ID NO: 8), and the Brichos domain of CTproSP-C from human (SEQ ID NO: 9).

In a preferred embodiment, the screening method is comprising the steps of:
a) providing an aqueous mixture comprising a known trimer/monomer ratio of the chaperone protein;
b) adding said one or more candidate compound(s) to the mixture;
c) allowing said one or more candidate compound(s) to interact with the chaperone protein in the mixture;
d) determining the trimer/monomer ratio of the chaperone protein in the mixture; and
e) concluding that said one or more candidate compound(s) is
  e1) active in the treatment of the condition if the trimer/monomer ratio of the chaperone protein is decreased in the presence of the candidate compound(s); or
  e2) not active in the treatment of the condition if the trimer/monomer ratio of the chaperone protein is not decreased in the presence of the candidate compound(s).

In one preferred embodiment, the screening method is further comprising determining whether the formation of fibrils of a fibrillating protein associated with the condition is decreased in the presence of the chaperone protein and said one or more active candidate compound(s), i.e. compared to the situation in the presence of the chaperone protein but absence of the candidate compounds(s). In a preferred embodiment, the screening method is comprising the further steps of:
f) providing a second aqueous mixture comprising the fibrillating protein and the chaperone protein;
g) adding said one or more candidate compound(s) considered active in step e1) to the second mixture to decrease the trimer/monomer ratio of the chaperone protein;
h) allowing the chaperone protein to interact with said one or more candidate compound(s) and with the fibrillating protein in the second mixture;
i) determining the formation of fibrils of the fibrillating protein in the second mixture; and
j) concluding that said one or more candidate compound(s) is
  j1) active in the treatment of the condition if the fibril formation of the fibrillating protein is decreased in the presence of the candidate compound(s); or
  j2) not active in the treatment of the condition if the fibril formation of the fibrillating protein is not decreased in the presence of the candidate compound(s).

According to a second aspect, the present invention provides use of trimers of a chaperone protein according to the invention as an in vitro target for candidate drugs for treatment of a condition associated with formation of amyloid protein fibrils in a mammal.

The present invention further provides according to a third aspect a compound or a combination of compounds, wherein said compound or combination is capable of decreasing the trimer/monomer ratio of a chaperone protein according to the invention for use as a medicament.

The present invention moreover provides according to a fourth aspect a monomer of a protein comprising more than or equal to 80 amino acid residues, and comprising an amino acid sequence having at least 70% identity to an amino acid sequence selected from the group consisting of residues 90-243 of Bri2 from human (SEQ ID NO: 2), the Brichos domain of Bri2 from human (SEQ ID NO: 3), residues 97-242 of Bri3 from human (SEQ ID NO: 5), the Brichos domain of Bri3 from human (SEQ ID NO: 6), CTproSP-C from human (SEQ ID NO: 8), and the Brichos domain of CTproSP-C from human (SEQ ID NO: 9), for use as a medicament.

According to a fifth aspect, the present invention provides a method of producing a pharmaceutical composition for treatment of a condition associated with formation of amyloid protein fibrils in a mammal, comprising the steps of:
 a) providing an active compound by
  a1) screening one or more candidate compound(s) for activity in the screening method according to the invention; or
  a2) utilizing the result of a previous screening procedure using the screening method according to the invention; and
 b) formulating the active compound with one or more suitable pharmaceutical ingredients to provide a pharmaceutical composition.

The present invention provides according to a sixth aspect a pharmaceutical composition comprising (i) a therapeutically effective amount of a monomer of a chaperone protein according to the invention and/or (ii) a therapeutically effective amount of a compound, or a combination of compounds, according to the invention, capable of decreasing the trimer/monomer ratio of said chaperone protein; and a suitable pharmaceutical carrier therefor.

According to a final aspect, the present invention provides a method of treating a condition associated with formation of amyloid protein fibrils in a mammal, including man, in need thereof comprising administration to and/or induction in said mammal of a therapeutically effective amount of a monomer of a chaperone protein according to the invention.

In preferred embodiments of the various aspects of the invention, the condition that is desirable to treat is selected from the group consisting of Alzheimer's disease, familial Danish dementia, familial British dementia and interstitial lung disease.

BRIEF DESCRIPTION OF THE DRAWINGS

FIG. 1 shows a schematic outline of Bri2 (SEQ ID NO: 1) processing.
FIG. 2 shows an alignment of some mammalian Bri2-Brichos amino acid sequences.
FIG. 3 shows a schematic outline of proSP-C (SEQ ID NO: 7) processing and an alignment of known mammalian CTproSP-C amino acid sequences.
FIG. 8 shows an alignment of the amino acid sequences of proSP-C BRICHOS and Bri2 BRICHOS.
FIG. 11 shows gel filtration of a mixture of Aβ40 and proSP-C BRICHOS, immediately after mixing and after 20 hours incubation.

LIST OF APPENDED SEQUENCES

Figure 4:
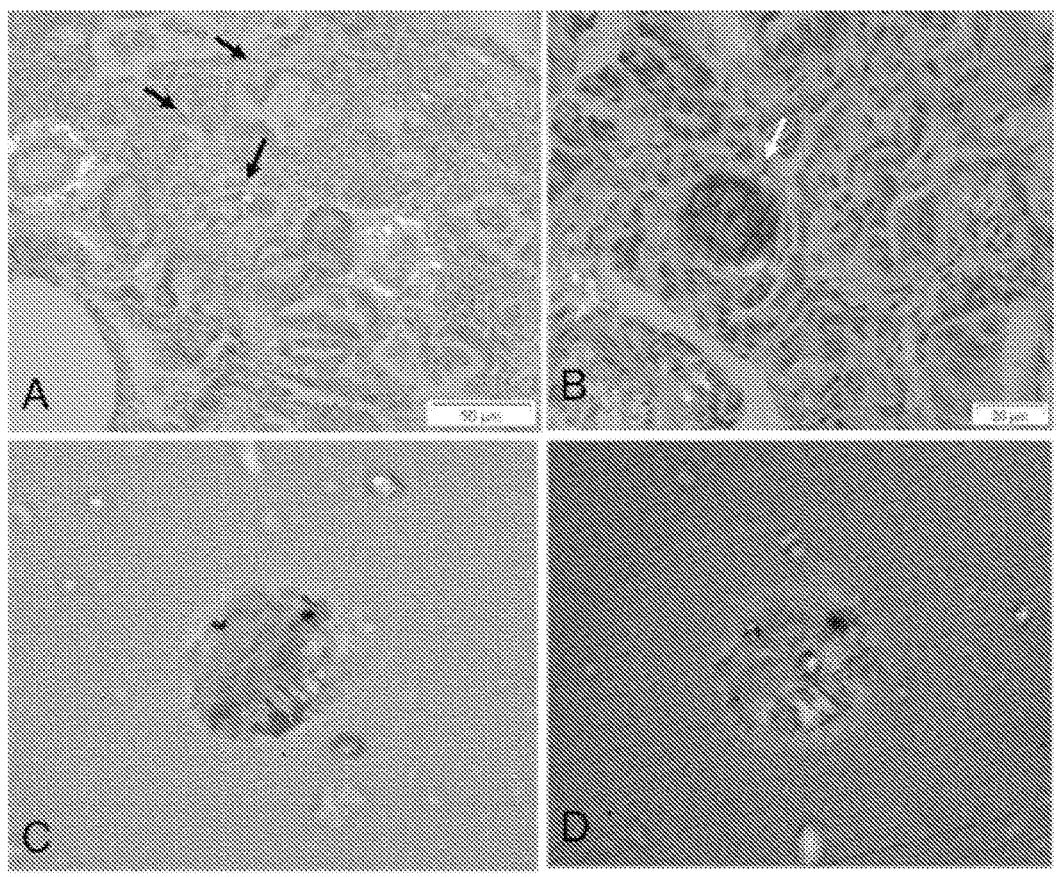
FIG. 4 shows stained amyloid deposits in lung tissue from ILD patients.

SEQ ID NO: 1 human Bri2
SEQ ID NO: 2 human Bri2(90-243)
SEQ ID NO: 3 human Bri2$_{Brichos}$ [Bri2(137-231)]
SEQ ID NO: 4 human Bri3
SEQ ID NO: 5 human Bri3(97-242)
SEQ ID NO: 6 human Bri3$_{Brichos}$ [Bri3(136-230)]
SEQ ID NO: 7 human proSP-C
SEQ ID NO: 8 human CTproSP-C [CTproSP-C(59-197)]
SEQ ID NO: 9 human CTproSP-C$_{Brichos}$ [CTproSP-C(90-197)]
SEQ ID NO: 10 human Aβ$_{1-40}$ peptide
SEQ ID NO: 11 human Aβ$_{1-42}$ peptide

DETAILED DESCRIPTION OF THE INVENTION

Bri2 (SEQ ID NO: 1), also referred to as integral membrane protein 2B (ITM2B), contains an evolutionary conserved Brichos domain spanning residues 137-231 (SEQ ID NO: 3). Based upon alignment with the Brichos domain of CTproSP-C determined herein (FIG. 8), the Brichos domain of Bri2 may alternatively be considered as spanning residues 131-231.

Bri2 is processed by furin in the C-terminal region, generating a 23-residue peptide (Bri23), and by the metalloprotease ADAM10, which causes a release of the Brichos-containing, extracellular domain from the N-terminal part of Bri. The Brichos domain is secreted into the extracellular space (L Martin et al., J Biol Chem 283: 1644-1652 (2008)). Thus, the furin/ADAM10 cleavage product is predicted as an endogenous species and useful as a chaperone protein in the context of the present invention. In Peng et al., Biochem. Biophys. Res. Commun., 393: 356-361 (2010), an extracellular domain of Bri2 spanning residues 90-236 binds to Aβ-peptide and prevents Aβ-peptide amyloid fibril formation. It is therefore predicted that each of Bri2(90-236) and Bri2(90-243) (SEQ ID NO:2) are useful as chaperone proteins according to the invention.

Bri3 (SEQ ID NO: 4), also referred to as integral membrane protein 2C (ITM2C), contains an evolutionary conserved Brichos domain spanning residues 136-230 (SEQ ID NO: 6). Based upon alignments with Bri2 and the Brichos domain of CTproSP-C determined herein (FIG. 8) and the close sequence similarity between Bri2 and Bri3, the Brichos domain of Bri3 may alternatively be considered as spanning residues 130-230. Based upon alignment with the Bri2 sequence of Peng et al., Biochem. Biophys. Res. Commun., 393: 356-361 (2010) with chaperone activity, the Bri3 sequence corresponding to Bri3(90-243) is spanning residues 97-242 (SEQ ID NO: 5). Both Bri2 and Bri3 are expressed in the central nervous system, including the brain. For instance, mature Bri2 is processed by the metalloprotease ADAM10, which causes a release of the Brichos-containing, extracellular domain from the N-terminal part. The Brichos domain is secreted into the extracellular space (L Martin et al., J Biol Chem 283: 1644-1652 (2008)).

Brichos domains contain about 100 amino acids and are found in several proteins associated with degenerative and proliferative diseases, such as Bri, associated with amyloid formation and familial British and Danish dementia, CA11 associated with stomach cancer, and proSP-C associated with lung disease, c.f. below. The name Brichos refers to identification of the domain in Bri, chondromodulin-1 related to chondrosarcoma and in lung surfactant protein C precursor (proSP-C) involved in respiratory disease. All of the so far identified Brichos-containing proteins are type II membrane proteins, and the Brichos domain is then located in the C-terminal, ER lumenal region, or secretory proteins that are translated into the ER lumen.

Lung surfactant protein C (SP-C) is a hydrophobic, acylated transmembrane peptide having 35 amino acid residues. It is synthesized as proprotein of 197 amino acid residues (a 191 aa variant is present in certain species including human), lung surfactant protein C precursor (proSP-C; SEQ ID NO: 7). ProSP-C is expressed only in lung alveolar type II epithelial cells and is anchored in the endoplasmic reticulum (ER) membrane protein with its C-terminal in the ER lumen. ProSP-C undergoes proteolytic cleavages (see FIG. 3), and the mature SP-C peptide corresponds to residues 24-58 of human proSP-C. SP-C and other protein and lipid components are secreted into the alveoli and are responsible for lowering the surface tension at the air/liquid interface, thereby preventing alveolar collapse at end expiration. As further illustrated in FIG. 3, the processing of proSP-C also produces a C-terminal fragment, the C-terminal domain of lung surfactant protein C precursor (CTproSP-C or CTC; SEQ ID NO: 8). The mature CTproSP-C protein corresponds to residues 59-197 of human proSP-C.

CTproSP-C (SEQ ID NO: 8) and hence also proSP-C contain a domain known as the Brichos domain (CTproSP-$C_{Brichos}$; SEQ ID NO: 9), corresponding to residues 90-197 of human proSP-C. It is also known that mutations in the Brichos domain are associated with lung disease, proSP-C misfolding and formation of intracellular aggregates. Elevated expression of proSP-C having a deletion of exon 4 (proSP-$C^{\Delta Exon4}$) produces a C-terminally shortened proprotein, resulted in lung dysmorphogenesis in transgenic mice and ER stress in transfected cells. Another mutation in the Brichos domain, resulting in the exchange of glutamine for leucine at position 188 in the proprotein (proSP-$C^{L188Q}$), is associated with dominantly inherited interstitial lung disease. Expression of the Brichos mutants proSP-$C^{\Delta Exon4}$ or proSP-$C^{L188Q}$ in lung-derived A549 cells or human embryonic kidney (HEK)293 cells results in increased formation of insoluble aggregates leading to apoptosis. In contrast, two other mutations, proSP-$C^{I73T}$ and proSP-$C^{E66K}$, localised in a region between the Brichos domain and the transmembrane domain (SP-C), are associated with altered intracellular trafficking but not aggregation. Thus, the Brichos domain in proSP-C and CTproSP-C is involved in prevention of (pro)SP-C aggregation. In one embodiment, the position corresponding to leucine-188 in human proSP-C is not glutamine. In a further embodiment, the position corresponding to leucine-188 in human proSP-C is strictly conserved. Obviously, the position corresponding to leucine-188 in human proSP-C has a different number in CTproSP-C (leucine-130 in human) and CTproSP-$C_{Brichos}$ (leucine-95 in human) as well as in certain other species.

Proteins containing the Brichos domain have been identified as chaperones, preventing the aggregation and fibrillation of proteins that are prone to fibrillation. The structure of the Brichos domain of CTproSP-C (CTproSP-$C_{Brichos}$) has now been determined. The distribution of conserved residues and mutations associated with interstitial lung disease, together with molecular dynamics simulations and hydrogen-deuterium exchange mass spectrometry, suggest how the Brichos domain mediates chaperone activity towards a common intermediate in amyloid formation. While it is known that proteins containing the Brichos domain have a tendency to form oligomers under physiological conditions, it has now been found that the dominant oligomer species under physiological conditions is the trimer. In the trimer, the putative active surface in each Brichos domain is embedded and consequently inactive. Altogether, it has now inventively been realized that the active oligomer species in proteins containing the Brichos domain is the monomer, and that promoting the monomeric over the trimeric form of proteins containing the Brichos domain improves their chaperone activity, i.e. is useful for decreasing or preventing the formation of aggregates and fibrils from proteins prone to form amyloid fibrils, such as Aβ, ABri, ADan and SP-C. Thus, it is the monomers of proteins comprising the Brichos domain of a mammalian Bri2 (ITM2B), Bri3, CTproSP-C and structurally similar proteins that have the capacity to decrease amyloid fibril formation and aggregation of Aβ-peptide, ABri/ADan and SP-C peptides.

The present invention provides according to a first aspect a method of screening one or more candidate compound(s) for activity in the treatment of a condition associated with formation of amyloid protein fibrils in a mammal, or amyloidosis. Throughout the present disclosure and the various aspects of the invention, it is generally preferred that the condition is selected from the group consisting of Alzheimer's disease, familial Danish dementia, familial British dementia and interstitial lung disease. A specifically preferred condition is Alzheimer's disease. The screening method involves determining whether the trimer/monomer ratio of a chaperone protein is decreased in the presence of said one or more candidate compound(s).

The chaperone protein is preferably including a Brichos domain. The chaperone protein is typically comprising more than or equal to 80 amino acid residues. It is comprising an amino acid sequence having at least 70% identity to an amino acid sequence selected from the group consisting of residues 90-243 of Bri2 from human (SEQ ID NO: 2), the Brichos domain of Bri2 from human (SEQ ID NO: 3), residues 97-242 of Bri3 from human (SEQ ID NO: 5), the Brichos domain of Bri3 from human (SEQ ID NO: 6), CTproSP-C from human (SEQ ID NO: 8), and the Brichos domain of CTproSP-C from human (SEQ ID NO: 9). This group includes endogenous cleavage products from Bri2, Bri3 and proSP-C, and their Brichos domains.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfil, instead of the specified percentage of identity, the corresponding percentage of similarity. Other alternative embodiments fulfil the specified percentage of identity as well as another, higher percentage of similarity, selected from the group of preferred percentages of identity for each sequence. For example, the isolated protein sequence may be 70% similar to another protein sequence; or it may be 70% identical to another sequence; or it may be 70% identical and furthermore 90% similar to another sequence.

For avoidance of doubt, the amino acid sequence having at least the given identity to the Brichos domain of the chaperone protein consists of more than or equal to 70, such as more than or equal to 80, such as more than or equal to 90 amino acid residues. A preferable size range is 70-100 amino acid residues, such as 80-100 amino acid residues, e.g. 90-100 amino acid residues.

It is noted that the Brichos domains of Bri2 from human, chimpanzee, bovine, pig, mouse and rat is highly conserved, see alignment in FIG. 2. Without desiring to be bound to any specific theory, it is contemplated that the Brichos domain harbours the desired activity with respect to the fibril-prone peptides. It is preferred that the chaperone protein according to the invention is selected from the group consisting of proteins comprising an amino acid sequence having at least 70%, such as at least 80%, preferably at least 90%, such as at least 95%, identity to any one of the Brichos domains of Bri2 from human (SEQ ID NO: 3), Bri3 from human (SEQ ID NO: 6) and proSP-C/CTproSP-C from human (SEQ ID NO: 9). In a preferred embodiment, the chaperone protein according to the invention contains all amino acid residues that are conserved in the Brichos domains of Bri2 from human, chimpanzee, bovine, pig, mouse and rat in FIG. 2. In specific embodiments, the chaperone protein according to the invention is selected from the group consisting of proteins comprising any one of the Brichos domains of Bri2 from human (SEQ ID NO: 3), Bri3 from human (SEQ ID NO: 6) and proSP-C/CTproSP-C from human (SEQ ID NO: 9).

For identifying compounds active against Alzheimer's disease, familial British Dementia or familial Danish dementia, it is preferred that the chaperone protein according to the invention is comprising an amino acid sequence having at least 70%, preferably at least 80%, more preferably at least 90%, such as at least 95% or even 100%, identity to an amino acid sequence selected from the group consisting of residues 90-243 of Bri2 from human (SEQ ID NO: 2), the Brichos domain of Bri2 from human (SEQ ID NO: 3), residues 97-242 of Bri3 from human (SEQ ID NO: 5), and the Brichos domain of Bri3 from human (SEQ ID NO: 6).

For identifying compounds active against interstitial lung disease, it is preferred that the chaperone protein according to the invention is comprising an amino acid sequence having at least 70%, preferably at least 80%, more preferably at least 90%, such as at least 95% or even 100%, identity to an amino acid sequence selected from the group consisting of CTproSP-C from human (SEQ ID NO: 8), and the Brichos domain of CTproSP-C from human (SEQ ID NO: 9).

In contrast to previous teachings, the isolated protein according to the invention is not comprising an amino acid sequence having at least 70% identity to residues 1-89 of Bri2 or 1-96 of Bri3 from human. In certain embodiments, the isolated protein according to the invention is not comprising an amino acid sequence having at least 50% identity to residues 1-89 of Bri2 or 1-96 of Bri3 from human. This implies that the isolated protein according to the invention contains a core amino acid sequence which displays a high similarity or identity to residues 90-243 of Bri2 or 97-242 of Bri3 from human and/or the Brichos domains of Bri2 or Bri3 from human (SEQ ID NOS: 2-3, 5-6) and optionally one or more other amino acid sequences, which other amino acid sequences may not display a high similarity or identity to residues 1-89 of Bri2 or Bri3 from human.

For avoidance of doubt, amino acid sequences that are shorter than 10 amino acid residues are not considered relevant in the context of being excluded from the isolated protein according to the invention. Thus, the isolated protein according to the invention is not comprising an amino acid sequence that consists of more than or equal to 10 amino acid residues having at least the given identity to residues 1-89 of Bri2 or Bri3 from human.

Furthermore, the isolated protein according to the invention is not comprising an amino acid sequence having at least 70% identity to residues 244-266 of Bri2 from human, i.e. human Bri23. In certain embodiments, the isolated protein according to the invention is not comprising an amino acid sequence having at least 50% identity to human Bri23. As set out above, this implies that the isolated protein according to the invention contains a core amino acid sequence which displays a high similarity or identity to residues 90-243 of Bri2 or 97-242 of Bri3 from human and/or a Brichos domain of Bri2 or Bri3, and optionally one or more other amino acid sequences, which other amino acid sequences may not display a high similarity or identity to human Bri23.

For avoidance of doubt, amino acid sequences that are shorter than 10 amino acid residues are not considered relevant in the context of being excluded from the isolated protein according to the invention. Thus, the isolated protein according to the invention is not comprising an amino acid sequence that consists of more than or equal to 10 amino acid residues having at least the given identity to human Bri23.

Proteins comprising a core amino acid sequence having one or more identities with Bri2, Bri3 or CTproSP-C target sequences as set out above may further comprise additional amino acid sequences which do not interfere with the chaperone function of the core amino acid sequence, i.e. interaction with the fibril-prone proteins. The additional amino acid sequences may be connected to the N-terminal of the core amino acid sequence, to the C-terminal of the core amino acid sequence, or both. It may also be connected via amino acid side chains, e.g. via a disulphide bond. The additional amino acid sequences may be essentially non-functional or may provide additional functionality to the resulting protein, e.g. solubility, stability or a desired affinity. Both the core amino acid sequence and any additional amino acid sequences may be chemically modified, including post-translational chemical modifications.

In one embodiment, the chaperone protein according to the invention is selected from the group of proteins consisting of an amino acid sequence having the identities set out above. That is, the chaperone protein consists of the desired core amino acid sequence having one or more identities with Bri2, Bri3 or CTproSP-C target sequences as set out above. The core amino acid sequence may be chemically modified, including post-translational chemical modifications.

In certain embodiments, the chaperone protein according to the present invention consists of less than or equal to 500, such as less than or equal to 250, such as less than or equal to 200, such as less than or equal to 150 or even 100 amino acid residues. In certain embodiments, the chaperone protein according to the present invention consists of more than or equal to 80, such as more than or equal to 90, such as more than or equal to 100 amino acid residues. A preferable size range is 80-200 amino acid residues, such as 90-150 amino acid residues, e.g. 90-100, 100-110, 90-110, 100-120, 110-120 or 90-120 amino acid residues.

In a preferred screening method, an aqueous mixture comprising a known trimer/monomer ratio of the chaperone protein according to the invention is provided. The trimer/monomer ratio is either determined immediately prior to each screening experiment or characterized once and for all prior for the given conditions prior to any screening experiments. Suitable methods for determining the trimer/monomer ratio include size exclusion chromatography, mass spectrometry, and ultracentrifugation. One or more candidate compound(s) is(are) added to the mixture. As the skilled person is well aware, the concentrations of the chaperone protein and/or the candidate compound(s) may be varied. The candidate compound(s) is(are) allowed to interact with the chaperone protein in the mixture. This typically implies allowing the components to interact for a period of time, e.g. from 1 s to 10 h, such as 1-60 min, under suitable conditions, e.g. at room temperature or approximately 37° C. The trimer/monomer ratio of the chaperone protein in the mixture is then determined and compared to the initial trimer/monomer ratio of the chaperone protein. Suitable methods for determining the trimer/monomer ratio include size exclusion chromatography, mass spectrometry, and ultracentrifugation. It is then concluded that the one or more candidate compound(s) is(are) active in the treatment of the condition if the trimer/monomer ratio of the chaperone protein has decreased. Alternatively, it is concluded that the one or more candidate compound(s) is(are) not active in the treatment of the condition if the trimer/monomer ratio of the chaperone protein has not decreased. The determination of whether a decrease of the trimer/monomer ratio of the chaperone protein has occurred or not implies a comparison compared to an untreated control, i.e. a chaperone protein which is not treated with any compound, or treated with a compound which is not the candidate compound(s). The untreated control may be performed in the same set of experiments or may be a previously determined reference value, gathered from earlier experiments, reports from others etc.

In a preferred screening method, compounds considered active in decreasing the trimer/monomer ratio of the chaperone protein are subjected to further testing, involving determining whether the formation of fibrils of a fibrillating, or fibril-prone, protein associated with the condition is decreased in the presence of the chaperone protein and the one or more active candidate compound(s). The determination of whether a decrease of the fibril formation of the fibrillating protein has occurred or not implies a comparison compared to an untreated control, i.e. a fibrillating protein in the presence of the chaperone protein, which is not treated with any further compound, or treated with a compound which is not the candidate compound(s). The untreated control may be performed in the same set of experiments or may be a previously determined reference value, gathered from earlier experiments, reports from others etc.

In one preferred screening method, a second aqueous mixture comprising the fibrillating protein and the chaperone protein is provided. As the skilled person is well aware, the concentrations of the fibrillating protein and/or the chaperone protein may be varied. The one or more candidate compound(s), which has (have) already been considered active in decreasing the trimer/monomer ratio of the chaperone protein, is (are) added to the second mixture in order to decrease the trimer/monomer ratio of the chaperone protein. As the skilled person is well aware, the concentration of the candidate compound(s) may be varied. The chaperone protein is allowed to interact with the one or more candidate compound(s) and with the fibrillating protein in the second mixture. This typically implies allowing the components to interact for a period of time, e.g. from 1 s to 10 h, such as 1-60 min, under suitable conditions, e.g. at room temperature or approximately 37° C. The formation of fibrils of the fibrillating protein in the second mixture is then determined. Suitable methods for determining the degree of fibrillation include microscopy and/or staining with dyes, e.g. with Congo Red, or fluorescing compounds, e.g. Thifloavin T (ThT). A suitable experiment for determining the degree of fibrillation is an aggregation kinetics experiments, in which the aggregation can be followed over time. It is then concluded that the one or more candidate compound(s) is (are) active in the treatment of the condition if the fibril formation of the fibrillating protein has decreased in the presence of the candidate compound(s). Alternatively, it is concluded that the one or more candidate compound(s) is (are) not active in the treatment of the condition if the fibril formation of the fibrillating protein has not decreased in the presence of the candidate compound(s). Determination of a decreased fibrillation thus involves a comparison to an untreated control, i.e. the degree of fibrillation by the fibrillating protein in the presence of the chaperone protein, but in the absence of the candidate compounds(s). Furthermore, a decreased fibrillation may involve prevention of fibrillation, dissolution of already formed fibrils, delaying the start fibril formation and/or retarding the progress of fibril formation.

In a preferred screening method, the fibrillating protein is selected from the group consisting of Aβ-peptide, ADan, ABri and SP-C. It is preferred that the fibrillating protein is Aβ-peptide.

The present invention provides according to a second aspect a novel use of trimers of a chaperone protein according to the invention as an in vitro target for candidate drugs for treatment of a condition associated with formation of amyloid protein fibrils in a mammal. As detailed hereinabove, a suitable candidate drug has the capacity to decrease the trimer/monomer ratio of the chaperone protein according to the invention. In a preferred embodiment, the candidate drugs are screened for activity in decreasing the trimer/monomer ratio of the chaperone protein.

The present invention provides according to a third aspect a compound or a combination of compounds, which are useful as medicaments. The compound or combination is capable of decreasing the trimer/monomer ratio of a chaperone protein, as can readily be verified by the screening method according to the invention. In a preferred embodiment, the compound(s) is (are) selected from the group consisting of antibodies and nucleic acid aptamers. The skilled person is well aware of methods for preparing antibodies, as well as nucleic acid aptamers, directed towards the trimer of the chaperone protein. In another preferred embodiment, the compound is bis-ANS (1,1'-bis (4-anilino-5,5'-naphthalenesulfonate)). In a preferred embodiment, the compound or a combination of compounds are useful for treatment of a condition associated with formation of amyloid protein fibrils in a mammal, preferably a condition is selected from the group consisting of Alzheimer's disease, familial Danish dementia, familial British dementia and interstitial lung disease. A specifically preferred condition is Alzheimer's disease.

The present invention provides according to a fourth aspect a monomer of a chaperone protein according to the invention, comprising more than or equal to 80 amino acid residues. The monomer of the chaperone protein is useful as a medicament, alone or in combination with other substances. The chaperone protein is comprising an amino acid sequence having at least 70% identity to an amino acid sequence selected from the group consisting of residues 90-243 of Bri2 from human (SEQ ID NO: 2), the Brichos domain of Bri2 from human (SEQ ID NO: 3), residues 97-242 of Bri3 from human (SEQ ID NO: 5), the Brichos domain of Bri3 from human (SEQ ID NO: 6), CTproSP-C from human (SEQ ID NO: 8), and the Brichos domain of CTproSP-C from human (SEQ ID NO: 9). In a preferred embodiment, the monomer of the chaperone protein is useful for treatment of a condition associated with formation of amyloid protein fibrils in a mammal, preferably a condition is selected from the group consisting of Alzheimer's disease, familial Danish dementia, familial British dementia and interstitial lung disease. A specifically preferred condition is Alzheimer's disease.

In one preferred embodiment, the amino acid sequence of the protein has at least 70% to an amino acid sequence selected from the group consisting of residues 90-243 of Bri2 from human (SEQ ID NO: 2), and the Brichos domain of Bri2 from human (SEQ ID NO: 3), with the provisos that said protein is not comprising an amino acid sequence having at least 70% identity to residues 1-89 of Bri2 from human; and said protein is not comprising an amino acid sequence having at least 70% identity to human Bri23, i.e. to residues 244-266 of Bri2 from human.

It is preferred that the chaperone protein is consisting of more than 90 amino acid residues and/or less than or equal to 200 amino acid residues, such as less than or equal to 150 amino acid residues.

In a preferred embodiment, the protein is selected from the group consisting of residues 90-243 of Bri2 from human (SEQ ID NO: 2), residues 97-242 of Bri3 from human (SEQ ID NO: 5), and CTproSP-C from human (SEQ ID NO: 8), corresponding to endogenous cleavage products from Bri2, Bri3 and proSP-C.

In one preferred embodiment, the protein is selected from the group consisting of the Brichos domains of Bri2 (SEQ ID NO: 3), Bri3 (SEQ ID NO: 6) and CTproSP-C (SEQ ID NO: 9) from human.

The present invention provides according to a fifth aspect a method of producing a pharmaceutical composition for treatment of a condition associated with formation of amyloid protein fibrils in a mammal. The method is comprising the step of providing an active compound. This may be achieved by screening one or more candidate compound(s) for activity employing the screening method according to the invention. Alternatively, the compound has already been identified in a previous screening of one or more candidate compound(s) for activity employing the screening method according to the invention. Regardless of what screening step is/has been involved, the active compound has the capacity to decrease the trimer/monomer ratio of the chaperone protein according to the invention. This may be achieved e.g. by stabilizing the monomer form, disrupting the trimer form, or a combination of the two. In the next step, the active compound is formulated with one or more suitable pharmaceutical ingredients, optionally including further active compounds, to provide a pharmaceutical composition. In particular, the composition may also include the chaperone protein according to the invention. Alternatively, the active compound may be directed towards the monomer or trimer of a chaperone protein according to the invention similar to what is already present in the relevant tissue, e.g. residues 90-243 of Bri2 (SEQ ID NO: 2) or residues 97-242 of Bri3 (SEQ ID NO: 5) in human brain tissue or CTproSP-C (SEQ ID NO: 8) in human lung tissue.

The present invention provides according to a sixth aspect a pharmaceutical composition comprising (i) a therapeutically effective amount of a monomer of a chaperone protein according to the invention and/or (ii) a therapeutically effective amount of a compound, or a combination of compounds, capable of decreasing the trimer/monomer ratio of the chaperone protein, and a suitable pharmaceutical carrier therefor. The pharmaceutical composition is useful as a medicament, preferably in treatment of a condition associated with formation of amyloid protein fibrils in a mammal. In a preferred embodiment, the pharmaceutical composition is useful for treatment of a condition selected from the group consisting of Alzheimer's disease, familial Danish dementia, familial British dementia and interstitial lung disease. A specifically preferred condition is Alzheimer's disease.

The present invention also provides a novel use of (i) a monomer of a chaperone protein according to the invention, and/or (ii) a compound or a combination of compounds according to the invention, that is capable of decreasing the trimer/monomer ratio of the chaperone protein, for use in treatment of a condition associated with formation of amyloid protein fibrils in a mammal.

The chaperone proteins and compounds according to the invention can be incorporated into pharmaceutical compositions. Such compositions typically include the chaperone proteins and/or compounds according to the invention and a suitable pharmaceutically acceptable carrier. As used herein, a "suitable pharmaceutical carrier" includes solvents, dispersion media, coatings, isotonic and absorption delaying agents, and the like, that are compatible with pharmaceutical administration. Supplementary active compounds can also be incorporated into the compositions.

A pharmaceutical composition is formulated to be compatible with its intended route of administration. Examples of routes of administration include parenteral (e.g. intravenous, intradermal, subcutaneous), oral, intranasal (e.g. inhalation), transdermal, transmucosal, intrathecal, intracerebral ventricular (e.g. using an Omaya reservoir-shunt with in-line filter that is surgically placed into the cisternal space), and rectal administration.

Potentially useful parenteral delivery systems for a composition include slow-dissolving polymer particles, implantable infusion systems, and liposomes. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Treatment of the conditions Alzheimer's disease, familial Danish dementia, familial British dementia and interstitial lung disease may also be effected by direct delivery of the chaperone proteins and compounds according to the invention to the relevant tissue, i.e. the central nervous system, preferentially to the brain, or the lung tissue.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating on particles of the isolated protein according the invention (e.g. lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Example of such agents include sugars, polyalcohols such as mannitol and sorbitol, and sodium chloride. Prolonged absorption of the injectable compositions can be brought about by including in the composition an agent which delays absorption, for example, aluminum monostearate or gelatin.

Sterile injectable solutions can be prepared by incorporating the chaperone proteins and/or compounds according to the invention in the required amount in an appropriate solvent with one or a combination of ingredients enumerated above, as required, followed by filtered sterilization. Generally, dispersions are prepared by incorporating the chaperone proteins and/or compounds according the invention into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the chaperone proteins and/or compounds according the invention plus any additional desired ingredient from a previously sterile-filtered solution thereof.

Oral compositions generally include an inert diluent or an edible carrier. For the purpose of oral therapeutic administration, the chaperone proteins and/or compounds according the invention can be incorporated with excipients and used in the form of tablets, troches, or capsules, e.g., gelatin capsules.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, e.g. for treatment of interstitial lung disease, the chaperone proteins and/or compounds are delivered in the form of an aerosol spray from pressured container or dispenser that contains a suitable propellant, e.g. a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the chaperone proteins and/or compounds according the invention are formulated into ointments, salves, gels, or creams as generally known in the art.

The chaperone proteins and/or compounds according the invention can also be prepared in the form of suppositories (e.g. with conventional suppository bases such as cocoa butter and other glycerides) or retention enemas for rectal delivery.

In one embodiment, the chaperone proteins and compounds according the invention are prepared with a carrier that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to tissued specifically affected by Alzheimer's disease, familial Danish dementia, familial British dementia and interstitial lung disease with monoclonal antibodies) can also be used as pharmaceutically acceptable carriers. These can be prepared according to methods known to those skilled in the art.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of the isolated protein according the invention calculated to produce the desired therapeutic effect in association with the required pharmaceutical carrier.

Toxicity and therapeutic effects of the chaperone proteins and compounds according to the invention can be determined by standard pharmaceutical procedures in cell cultures or experimental animals, e.g. for determining the $LD_{50}$ (the dose lethal to 50% of the population) and the $ED_{50}$ (the dose therapeutically effective in 50% of the population). Suitable animal models can be used such as those described for amyloidoses in Sturchler-Pierrat et al, Rev Neurosci, 10: 15-24, 1999; Seabrook et al, Neuropharmacol 38: 1-17, 1999; DeArmond et al, Brain Pathology 5: 77-89, 1995; Telling, Neuropathol Appl Neurobiol 26: 209-220, 2000; and Price et al, Science 282: 1079-1083, 1998.

The dose ratio between toxic and therapeutic effects is the therapeutic index and it can be expressed as the ratio $LD_{50}/ED_{50}$. Chaperone proteins and/or compounds that exhibit high therapeutic indices are preferred. While chaperone proteins and/or compounds that exhibit toxic side effects may be used, care should be taken to design a delivery system that targets such proteins/compounds to the site of affected tissue in order to minimize potential damage to unaffected cells and thereby reduce side effects.

Data obtained from the cell culture assays and animal studies can be used in formulating a range of dosage for use in humans. The dosage of a chaperone protein and/or compound lies preferably within a range of circulating concentrations that include the $ED_{50}$ with little or no toxicity.

The dosage may vary within this range depending upon the dosage form employed and the route of administration utilized. For any chaperone protein and compound used in the method of the invention, the therapeutically effective dose can be estimated initially from cell culture assays in which, e.g. the rate of fibril formation or the rate of cell death is observed. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a chaperone protein according to the invention (i.e., an effective dosage) ranges from about 0.1 to 100 mg/kg body weight, more preferably about 1 to 100 mg/kg body weight, and even more preferably about 1 to 50 mg/kg body weight. The compound can be administered over an extended period of time to the subject, e.g., over the subject's lifetime. A dosage of 1 mg/kg to 100 mg/kg is usually appropriate, such as is the case for antibodies designated to act in the brain.

In some cases the chaperone proteins and/or compounds can be administered once per week for between about 1 to 10 weeks, preferably between 2 to 8 weeks, more preferably between about 3 to 7 weeks, and even more preferably for about 4, 5, or 6 weeks. The chaperone proteins and/or compounds can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a chaperone proteins and/or compounds can include a single treatment or, preferably, can include a series of treatments.

Chaperone proteins according to the invention for administration to mice expressing the human APP or to humans can be prepared in several ways. For increasing the likelihood of the proteins to pass the blood brain barrier (BBB) several methods are envisioned.

A couple of main strategies have emerged for drug passage through the BBB. They make use of endogenous transport systems, either by receptor-mediated transcytosis or by use of specific receptors, e.g. for glucose, amino acids or peptides. Peptides seem particularly attractive as vectors for carrying diverse cargos across the BBB. A number of different peptides have been shown to trigger endocytosis (typically by the LDL-receptor) and to be able to deliver a cargo across the BBB. Some of these peptides are amphiphilic positively charged cell penetrating peptides (CPPs, e.g. penetratin, ApoE derived peptide and other) but these can also be highly toxic at higher doses. Others like the synB family are also positively charged but without the hydrophobic part. A drawback of many of the endocytosis triggering peptides is that they, in order to be efficient, need be relatively large in order to form stable α-helices, which seems to correlate with efficient uptake. The advantage with delivery by transcytosis is that the cargo can be quite substantial and quite variable. A path where specific endogenous peptides, that have been shown to cross the BBB by a saturable transport system, would act as vectors for drug delivery is also a viable alternative. Several relatively short peptides of this kind, like MIF-1 (Pro-Leu-Gly, derived from oxytocin) and Peptide T (8 residues, derived from the HIV envelope) have been shown be efficiently transported across the BBB. See e.g. de Boer A G and Gaillard P J, Clin Pharmacokinet. 46:553-76, 2007; de Boer A G and Gaillard P J, Annu Rev Pharmacol Toxicol. 47:323-55, 2007; Pardridge W M, Drug Discov Today. 12:54-61, 2007, for descriptions of methods for delivery across the BBB. In the present case, it is envisioned that said peptides or proteins can be mixed with the chaperone proteins, or alternatively they can be expressed covalently linked to the chaperone proteins.

In other formulations, the chaperone proteins can be linked to nanoparticles for delivery across the BBB (Lockman P R et al., Drug Dev Ind Pharm. 28:1-13, 2002; Tosi G et al., Expert Opin Drug Deliv. 5:155-74, 2008).

Modifications such as lipidation can also be used to stabilize proteins and to enhance uptake and tissue penetration (e.g., into the brain). A method for lipidation of antibodies is described by Cruikshank et al, J Acquired Immune Deficiency Syndromes Hum Retrovirol 14: 193, 1997.

When a chaperone protein and/or compound according to the invention is to be administered to an animal (e.g. a human) to treat Alzheimer's disease, familial Danish dementia, familial British dementia or interstitial lung disease, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific chaperone protein and/or compound employed, the age, body weight, general health, gender, and diet of the subject, the time of administration, the route of administration, the rate of excretion, any drug combination, and the degree of expression or activity to be modulated.

The pharmaceutical compositions of the invention can be included in a container, pack, or dispenser together with instructions for administration. For example, the instructions can include directions to use the composition to treat an individual having or at risk for Alzheimer's disease, familial Danish dementia, familial British dementia or interstitial lung disease.

According to a final aspect, the present invention provides a method of treating a condition associated with formation of amyloid protein fibrils in a mammal, including man, in need thereof. The method is comprising administration to and/or induction in said mammal of a therapeutically effective amount of a monomer of a chaperone protein according to the invention. As indicated hereinabove, this may be achieved by administration of a therapeutically effective amount of a monomer of a chaperone protein according to the invention. Alternatively, it may be achieved by administration of a therapeutically effective amount of a compound, or a combination of compounds, according to the invention, that is capable of decreasing the trimer/monomer ratio of the chaperone protein. It may also be achieved by co-administration of a therapeutically effective amount of a chaperone protein according to the invention and a therapeutically effective amount of a compound, or a combination of compounds, according to the invention, wherein the compound(s) are capable of decreasing the trimer/monomer ratio of the chaperone protein.

These active chaperone proteins and/or compound(s) capable of decreasing the trimer/monomer ratio of the chaperone protein may be delivered in the form of a pharmaceutical composition according to the invention.

In a preferred embodiment, the pharmaceutical composition is useful for treatment of a condition selected from the group consisting of Alzheimer's disease, familial Danish dementia, familial British dementia and interstitial lung disease. A specifically preferred condition is Alzheimer's disease.

In one preferred embodiment, the treatment is selected from the group consisting of preventive, palliative and curative treatment.

The present invention provides for both prophylactic and therapeutic methods of treating a subject at risk of (or susceptible to) Alzheimer's disease, familial Danish dementia, familial British dementia or interstitial lung disease. As used herein, the term "treatment" is defined as the application or administration of a chaperone protein and/or a compound according to the invention to a patient, or application or administration of a chaperone protein and/or compound according to the invention to an isolated tissue or cell line from a patient, who has Alzheimer's disease, familial Danish dementia, familial British dementia or interstitial lung disease, a symptom of disease or a predisposition toward a disease, with the purpose to cure, heal, alleviate, relieve, alter, remedy, ameliorate, improve or affect the disease, the symptoms of disease or the predisposition toward disease.

In one aspect, the invention provides a method for preventing a disease or condition (i.e., decreasing the risk of contracting, or decreasing the rate at which symptoms appear that are associated with a disease or condition) associated with fibril formation caused by Aβ peptide and/or ABri/ADan peptide and/or SP-C by administering to the subject a chaperone protein and/or a compound according to the invention that reduces aggregation of the polypeptide. Subjects at risk for Alzheimer's disease, familial Danish dementia, familial British dementia or interstitial lung disease can be identified by, for example, any or a combination of appropriate diagnostic or prognostic assays known in the art. Administration of a prophylactic agent can occur prior to the manifestation of symptoms characteristic of the disease, such that the disease is prevented or, alternatively, delayed in its progression.

The chaperone proteins and compounds according to the invention can be administered to a patient at therapeutically effective doses to prevent, treat or ameliorate disorders involving fibril formation associated with Alzheimer's disease, familial Danish dementia, familial British dementia or interstitial lung disease. A therapeutically effective dose refers to that amount of the compound sufficient to result in amelioration of symptoms of the disorders. Toxicity and therapeutic efficacy of such compounds can be determined by standard pharmaceutical procedures as described above.

It is also contemplated that the chaperone proteins according to the invention can be administered by gene therapy, such as by using expression vectors, plasmids or viruses to transfect cells in the neural system, preferably brain, such that the protein is expressed by these cells in the central neural system. This is useful for the treatment of Alzheimer's disease, familial Danish dementia or familial British dementia. The corresponding expression may be achieved in lung tissue in the case of interstitial lung disease.

The present invention will now be further illustrated by the following non-limiting examples.

In the Examples and the Drawings, the C-terminal part of proSP-C is interchangeably termed either CTproSP-C or CTC (SEQ ID NO: 8).

EXAMPLES

Example 1

ILD with proSP-C Mutations in Amyloid Disease

Molecular chaperones have been implicated as potent modulators of protein misfolding diseases, including amyloidoses, but examples where improper chaperone function results in disease have not been described. Recombinant CTC (CTproSP-C) binds to peptides derived from the TM region of proSP-C, thereby preventing β-sheet aggregation and fibril formation. More than 50 different mutations in the proSP-C gene (SFTPC) have been found in patients suffering from interstitial lung disease (ILD). Interestingly, only five of these are found in the mature TM SP-C helix, whereas the vast majority are located in the linker and in the BRICHOS domain. The first half of the linker region is highly conserved through evolution, but its function is not known.

Lung tissue obtained at lung transplantation (n=6) or autopsy (n=1) of children with endstage ILD due to a mutation in SFTPC was analysed histologically for the presence of amyloid (Table 1). Amyloid disease is defined by the presence of deposits that stain with Congo red and show apple green birefringence under polarized light. In all but one ILD case, amyloid deposits with typical staining properties were identified (FIG. 4 and Table 1). The amyloid appeared as small irregular deposits, most commonly interstitially but sometimes in alveolar lumina. The latter deposits were often roundish.

TABLE 1

Histological analysis for presence of amyloid

| SFTPC mutation | Race | Sex | Age at onset | Age at transplant | Histologic description | Amyloid | IHC mature SP-C |
|---|---|---|---|---|---|---|---|
| I73T | C | M | 2 mo | 6 ys | IP with fibrosis | ++ | + |
| I73T | C | F | 3 mo | 5 ys | (IP on biopsy 5 mo) Explant: IP and fibrosis | ++ | + |
| H64P | C | F | 1 mo | Expired 12 ys, waiting | IP, chronic inflammation | − | NS |
| Δ91-93 | C/NA | F | 3 mo | 14 mo | ATII hyperplasia, alv proteinosis | + | + |
| I73T | C | F | 4 mo | 12 ys | Interstitial inflam., fibrosis, remodeling Biopsy: alveolar proteinosis | + | NS |
| I73T | B | F | 8 mo | 2 ys | Biopsy: pulmonary hemosiderosis Explant: organizing IP | + | NS |
| c.494_5delA | C | M | 2 mo | 12 mo | Explant: IP and fibrosis | + | NS |

C = Caucasian;
B = Black;
NA = Native American;
ATII, alveolar type II cell;
IP, interstitial pneumonitis;
ED, European descent;
IHC, immunohistochemistry;
NS, not analyzed.

Histological Examination and Light and Electron Microscopy of Fibrils

Ten μm thick lung tissue sections were deparaffinized, stained with Congo red and examined for amyloid in a polarization microscope. The very pronounced chronic inflammation may raise the question whether observed amyloid deposits could be of acute phase serum protein A (AA) origin, and therefore sections were immunolabelled with antibodies against protein AA. Other sections from all the materials containing amyloid deposits were immunolabelled with rabbit antiserum against mature SP-C, the N-terminal propeptide segment of proSP-C, or CTC. After development with 3,3'-diaminobenzidine tetrahydrochloride, the immunolabelled sections were stained with Congo red solution for the simultaneous detection of amyloid and immunoreactivity. A synthetic peptide corresponding to residues 24-45 of human proSP-C was incubated for seven days at 200 μM concentration in 10% aqueous formic acid at 37° C. with shaking. Droplets (0.8 microliter) were applied to microscopical slides, air dried and stained with Congo red B solution. After mounting under cover slips, the materials were examined in a polarization microscope for Congophilia and green birefringence. For electron microscopy, aliquots of 2 μl were adsorbed for 1 min on 200-mesh copper grids and stained with 2% uranyl acetate in 50% aqueous ethanol for 30 s before being examined and photographed using a Hitachi H7100 microscope operated at 75 kV.

Immunolabeling experiments were performed on three materials with amyloid associated with the proSP-C mutations I73T and Δ91-93. Antibodies against mature SP-C labeled the tissue diffusely but unevenly and not only alveolar epithelium. Double staining with Congo red was necessary to identify the small amyloid deposits, which for all three cases showed a clearcut but somewhat uneven immunolabeling (FIG. 4 and Table 1).

FIG. 4 shows amyloid in lung tissue. Small distinct amyloid deposits were identified in 6 out of 7 ILD specimens. As shown in FIG. 4A, the amyloid was strongly stained with Congo red and showed a bright green birefringence in polarized light (arrows). In FIG. 4B an amyloid deposit was labeled with an antibody against mature SP-C, visualized with 2,2'-diamino benzidine and then stained with Congo red and examined in polarized light. Staining with Congo red is evident in the periphery of the deposit (arrow). FIG. 4C shows Congo red stained fibrils of synthetic proSP-C(24-45). FIG. 4D shows the same material as in FIG. 4C, but visualized between crossed polars.

Preabsorption with peptide corresponding to proSP-C residues 24-45 abolished all immunoreactivity. Antibodies against the N-terminal segment of proSP-C, or against CTC, labeled alveolar epithelium strongly in some areas, but the amyloid deposits were completely non-reactive. Incubation with antibodies against the acute phase serum protein AA, which forms amyloid secondary to chronic inflammatory states, showed no immunoreactivity in any case.

Further support for the notion that SP-C can form amyloid comes from in vitro studies showing that mature SP-C peptide (corresponding to residues 24-58 in proSP-C forms amyloid-like fibrils as judged by electron microscopy. Incubation of a synthetic peptide corresponding to the first 21 residues of mature SP-C (i.e. proSP-C residues 24-45), results in formation of amyloid-like fibrils, as judged by light microscopy after staining with Congo red (FIG. 4), and electron microscopy (not shown).

These results show that ILD due to mutations in CTC is associated with formation of amyloid, and that the region that forms amyloid deposits is derived from the mature SP-C region, localized outside CTC. The small amounts of amyloid detected are not likely pathogenic as such. However, these deposits may indicate the presence of toxic oligomers. It is likely that cytotoxicity in amyloid disease is mainly caused by prefibrillar, soluble oligomers, which are not detected by amyloid staining procedures.

Example 2

Hydrogen Deuterium Exchange (HDX) Studies of CTproSP-C and proSP-C$_{Brichos}$

Hydrogen Deuterium Exchange (HDX)

Hydrogen deuterium exchange coupled to mass spectrometry (HDX-MS) gives information about structural dynamics by measurement of deuterium incorporation into the protein backbone amides. Flexible or solvent-exposed segments allow rapid exchange, while less exposed or tightly folded segments exchange more slowly. The various degrees of deuterium incorporation in the different protein regions were determined using peptic digestion and LC-MS analysis.

Deuterated buffers were prepared by three rounds of freeze-drying of the 1 M stock Tris buffer, pH 8, and reconstitution in 99.9% $D_2O$ (Cambridge Isotopes, Andover, Mass.) to a final Tris concentration of 20 mM. To start the incubation at 22° C., CTC (CTproSP-C) stock solution with a concentration of 0.9 mM was diluted in deuterated Tris buffer to a final deuterium content of 92.5%. For CTC/peptide and proSP-C BRICHOS/peptide interaction studies, KKV$_7$KK (SEQ ID NO:12), KKV$_5$KK (SEQ ID NO:13), or KKA$_7$KK (SEQ ID NO:14) were pre-incubated with either Tris buffer or proteins, for 10 min at 22° C., and subsequently diluted in deuterated Tris buffer. Final concentrations were 30 µM CTC or proSP-C BRICHOS and 40 µM peptide. The deuterium content was 92.5%. Aliquots of 20 µl were collected in triplicates from three separate incubations after 1, 5, 10, 30, and 60 min. Fully deuterated protein was prepared by freeze-drying a sample of CTC, followed by resuspension in 99.9% $D_2O$ and incubation for 4 h at 50° C. Deuterium exchange was quenched by transferring aliquots to pre-chilled Eppendorf tubes containing 0.5 µL 5% trifluoroacetic acid (TFA) (Merck, Darmstadt, Germany), vortexing, and freezing in liquid nitrogen. Samples were kept in liquid nitrogen until analyzed.

Mass Spectrometry

Aliquots of deuterated CTC were thawed and injected into an HPLC system using a pre-chilled Hamilton syringe. The system was submersed in an ice bath during analysis. Protein samples were injected into a 5 µl sample loop and digested online in a Porozyme Immobilized Pepsin Cartridge (Applied Biosystems, Foster City, Calif.), operated at 17 µl/min in 0.05% TFA. Peptic peptides were desalted using a Waters Symmetry C$_{18}$ trap column and eluted in a single step with 70% acetonitrile containing 0.1% formic acid at a flow rate of 17 µl/min. Digestion and desalting was carried out for 10 min. Samples were delivered to the mass spectrometer through a tapered tip emitter with an opening of 50 µm (New Objective, Milford, Mass.) coupled to the HPLC via a T-connector.

Spectra were acquired in the positive-ion mode with a Waters Ultima API mass spectrometer (Waters, Milford, Mass.) equipped with a Z-spray source. The source temperature was 80° C., the capillary voltage 1.7 kV and the cone and RF lens 1 potentials were 100 and 38 V, respectively. The mass spectrometer was operated in single-reflector mode with a resolution of 10 000 (full width half maximum definition). The mass scale was calibrated using [Glu1]-fibrinopeptide B. Scans were acquired for 5 min at a rate of one scan per 2 sec between 300 and 2000 m/z. Peptic peptides were identified based on a map of pepsin-digested undeuterated protein, using automated LC-MS/MS analysis with a Waters NanoAcquity system (Waters, Milford, Mass.). Peptide sequences were identified by individual analysis of collision-induced dissociation spectra using the Waters MassLynx and ProteinLynx software packages.

Deuteration rates were determined by calculation of the average and standard deviation of the m/z values of the isotope envelope centroids from experimental triplicates using the Waters MassLynx software package. Deuteration curves were fitted for one-phase association (where maximum deuteration was reached at the first time point) or two-phase association (where a time-dependent increase could be observed), using the GraphPad Prism software (GraphPad Software Inc., La Jolla, Calif.). Rate constants were calculated in deuterons/min.

Figure 5A:
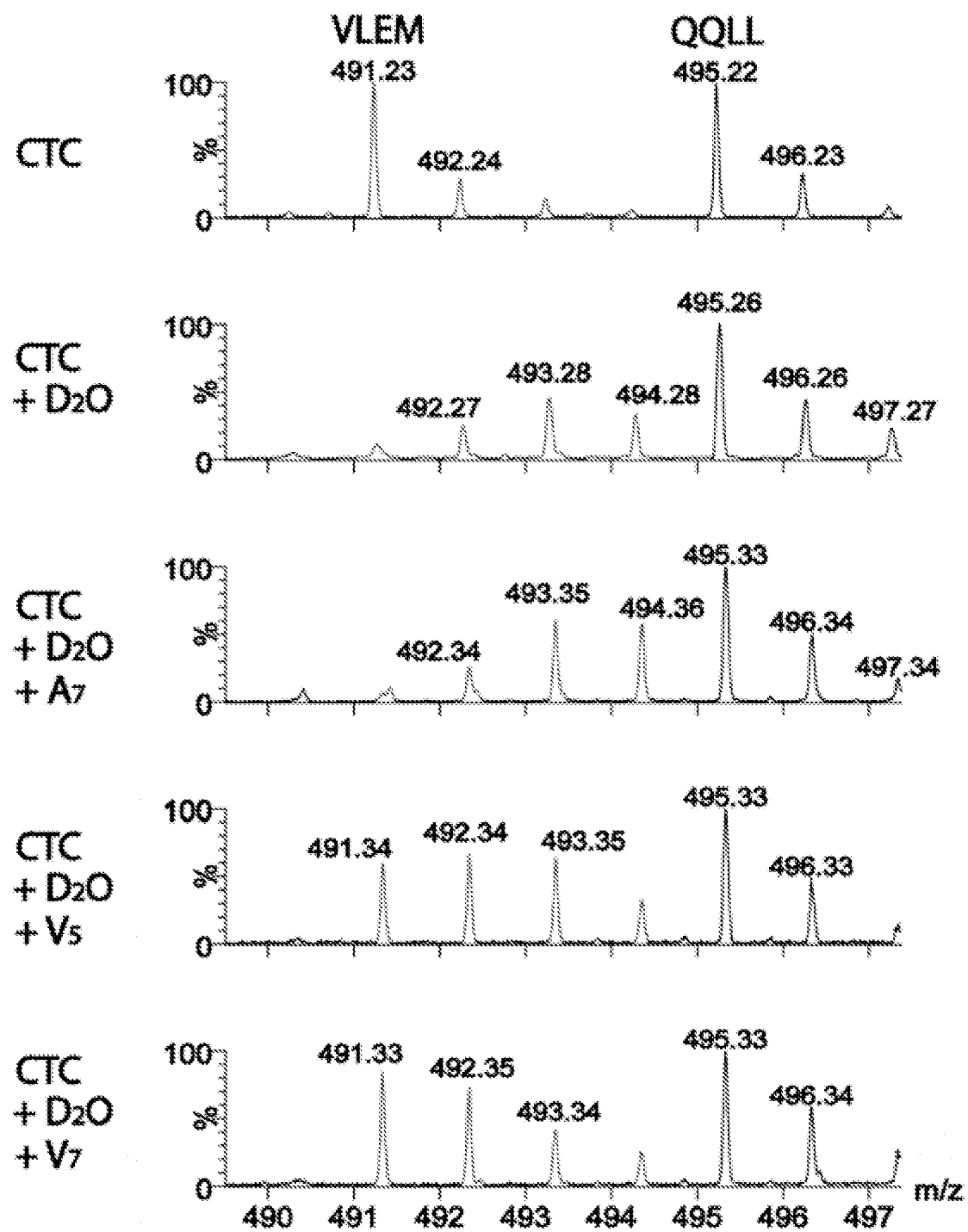
FIG. 5 shows mass spectra of CTproSP-C (CTC) in the presence of substrate-like peptides and of the peptides themselves.
Figure 5B:
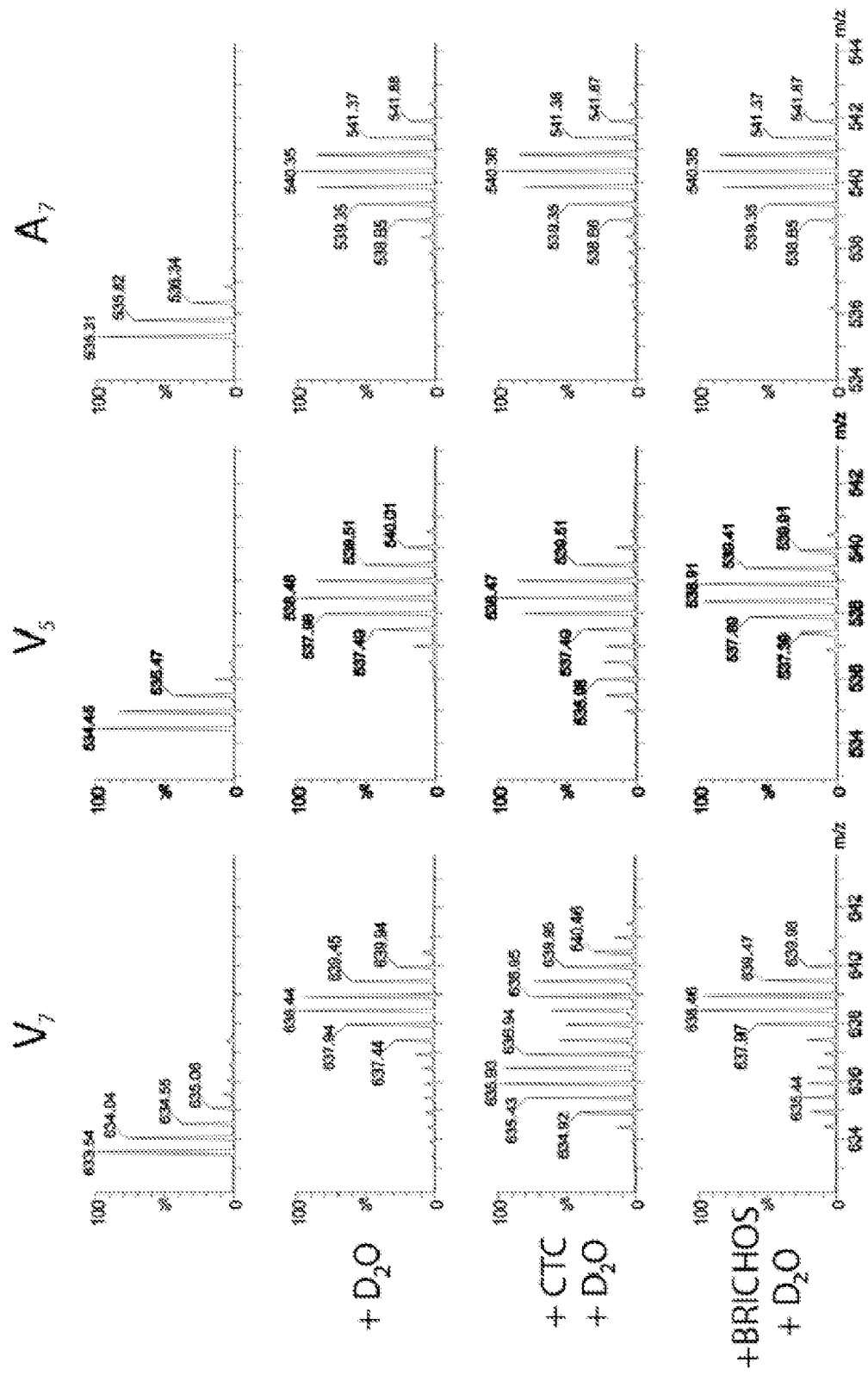

The mass spectra of CTproSP-C (CTC) in the presence of substrate-like peptides and of the peptides themselves in FIG. 5 indicate that the linker region stabilizes substrate peptides bound to BRICHOS. In FIG. 5A, the spectra correspond, from top to bottom, to CTC that is (i) undeuterated, (ii) deuterated for 1 min, (iii) deuterated in the presence of the A7 peptide, (iv) the V5 peptide, and (v) the V7 peptide. The VLEM fragment (residues 68-71) is rapidly deuterated in absence of a peptide ligand, indicating no stable secondary structure. The presence of a poly-valine peptide reduces deuterium labeling, while poly-alanine fails to protect the VLEM fragment. The QQLL fragment (residues 107-110, black) is not affected by the presence of any of the peptides. FIG. 5B shows mass spectra of V7, V5 and A7 peptides before deuteration (first row), after deuteration on their own (second row), after deuteration in the presence of CTC (third row), and after deuteration in the presence of BRICHOS (last row).

Interestingly, both the BRICHOS mutation Δ91-93 and the linker mutation I73T give rise to amyloid deposits with similar immunoreactivity (FIG. 4), indicating lack of proper chaperoning of the proSP-C TM segment in association with both of these mutations. In CTC, the linker region is flexible and lacks ordered secondary structure as judged by HDX-MS. However, a part of the linker region (residues 68-71) shows a significant decrease in deuteration of backbone amide hydrogens upon addition of the substrate peptides KKVVVVVVVKK (referred to as V$_7$) or KKVVVVVKK (V$_5$). No such effect is observed in the presence of the non-substrate peptide KKAAAAAAAKK (A$_7$) (FIG. 5A). Correspondingly, V$_7$ and V$_5$, but not A$_7$, become protected against HDX in the presence of CTC. In the presence of proSP-C BRICHOS (which binds substrate peptides in a similar way as CTC), however, only weak protection of substrate peptides is seen (FIG. 5B). Co-incubation of a free peptide corresponding to the linker region and V$_7$ did not result in any effect on deuteration of any of the peptides. These data indicate that the linker region interacts with peptides bound to proSP-C BRICHOS so that in proSP-C, the linker region docks to the BRICHOS-bound TM region, thus forming a strand-loop-strand structure. This would explain how mutations in the linker region as well as in the BRICHOS domain can be associated with ILD and amyloid formation.

Example 3

Structure of the Brichos Domain of proSP-C

Circular Dichroism (CD) Spectroscopy

CD spectra in the far-UV region (190-260 nm) were recorded at 22° C. with a Jasco J-810-150S spectropolarimeter (Jasco, Tokyo, Japan) using a bandwidth of 1 nm and a response time of 2 s, and 10 data points/nm were collected. The spectra shown are averages of three scans. Spectra were recorded for CTC (CTproSP-C; 15 µM) and trypsin-treated CTC (10 µM).

Mass Spectrometric Analysis of Trypsin-Treated CTC

Cleavage sites in trypsin-treated CTC were determined by dissolving the protein in 30% acetonitrile/0.1% formic acid, followed by MS analysis. A fragment with an average molecular weight of 11 540 Da was observed, indicating that the cleaved protein encompasses residues 82-160 and 168-197, linked by a disulfide bridge between Cys121 and Cys189 (theoretical average molecular weight: 11541 Da).

Crystallization

Crystals suitable for structure determination were obtained within weeks by means of in situ proteolysis with trypsin. MS analysis suggests that the crystallized material corresponds to residues 82-160 and 168-197 of proSP-C. The structure presented herein was derived from crystals of seleno-methionylated protein, obtained using the sitting-drop method at 293 K and 277 K, in various concentrations ranging between 0.3-0.7 mM. A single crystal belonging to space group C2 (a=132.05 Å, b=39.33 Å, c=114.76 Å, β=99.6°) was grown from 0.1 M Bis-Tris pH 6.5 and 20% (w/v) PEG MME 5K. The crystal was soaked in 30% (w/v) PEG 400, flash-frozen in liquid nitrogen and used for data collection.

Data Collection, Processing, Scaling and Structure Determination

Data to 2.1 Å were collected at the European Synchrotron Radiation Facility, France, using an ADSC Q315 detector on the ID23eh1 beam line. All data were processed in MOSFLM12 and scaled in SCALA13. Data are essentially 100% complete to 2.3 Å Bragg spacing, then drop off rapidly and are only ~60% complete in the outer resolution shell to 2.1 Å.

The crystal used for structure determination contained two proSP-C BRICHOS trimers per asymmetric unit. The structure was phased using the Multiple Anomalous Dispersion (MAD) technique with data collected at three different wavelengths, corresponding to the selenium atom peak, inflection point and high-energy remote, respectively.

Initial phases to 2.9 Å were estimated using SHARP, where 18 seleno-methionine sites were identified. Phases were subsequently improved and extended to 2.1 Å by using dm to perform density modification (solvent flattening, averaging, histogram matching). Non-crystallographic symmetry (NCS) operators and monomer envelope for averaging were obtained from a preliminary model traced in an initial 2.8 Å map and refined using tight 6-fold NCS restraints.

Model Building, Refinement and Validation

A model for one subunit was built in the averaged map and used to create the other five NCS-related subunits. Refinement and rebuilding was done using the peak (pk) wavelength data and carried out using a combination of Coot, O, Refmac5, Buster, and Phenix.

The electron density maps resulting from MAD phasing based on 18 selenium sites allowed us to model all residues in the proSP-C BRICHOS domain except residues 152-179, located between α1 and α2 (FIG. 6) and encompassing the peptide 161-167 removed by trypsin cleavage during crystallization. The missing segment was identified as disordered by HDX-MS and is strongly predicted to lack secondary structure. It is also the region with the highest sequence variability and difference in length between different species. Taken together, these data suggest that the residues between the two helices constitute a natively disordered segment that is not needed for the structural integrity of the protein. Intact CTC and trypsin-cleaved CTC both bind the substrate peptide VVV equally well. Hence, the crystallized protein is structurally and functionally similar to wt material.

It is clear that the N-terminal part of the crystallized protein is structurally adaptable, and that it follows quite different paths in these two copies. Hence, this region of proSP-C should be considered part of the linker region preceding the BRICHOS domain proper, which we define as residues 90-197.

The final model consists of 470 amino acid residues (residues 89-149 and 180-197 in chain A, 82-149 and 181-197 in chain B, 88-151 and 180-197 in chain C, 89-148 and 180-197 in chain D, 89-125, 132-149 and 181-197 in chain E, 88-148 and 181-197 in chain F, and 137 water molecules. 19 protein residues have been modeled with alternate conformations. All of the modelled chains can be pair-wise superimposed with r.m.s.d. of 0.6±0.1 Å for 76 superimposed Cα atoms.

The two trimers in the asymmetric unit of our crystals are essentially identical (r.m.s.d. 0.574 Å for 462 superimposed Cα atoms). The observed trimer is formed by close packing of the β1 strands from each subunit around the central three-fold axis, and head-to-tail interactions between α1 and α2# (# indicates that the structural element is from a neighboring subunit in the trimer). A number of inter-subunit salt bridges and hydrogen bond interactions provide directionally specific interactions (Table 2).

TABLE 2

Hydrogen bond interactions and salt bridges in the trimer interface

| Subunit 1[#]<br>Residue atom (location) | Subunit 2[#]<br>Residue atom (location) |
|---|---|
| Thr93 Oγ1 (β1) | Thr93 O1 (β1) |
| Lys114 Nζ (β3) | Glu135 Oε2 (α1) |
| Gly118 N (β3-β4) | Glu135 Oε2 (α1) |
| Thr187 Oγ1 (α2) | Tyr106 OH (β2) |
| Thr187 O1 (α2) | Leu134 N (β4-α1) |
| Glu191 Oε1 (α2) | Arg139 NH1/NH2 (α1) |
| Glu191 Oε1 (α2) | Ser133 Oγ1 (β4-α1) |

[#]Arbitrary subunit names

The trimer interface is largely hydrophobic (66% of the buried surface area) and approximately 24% of the total subunit accessible surface area (1150 Å$^2$ per subunit) is buried in the trimer. This is well within the range of protein-protein interaction surfaces observed in multimeric proteins.

All residues are within the allowed regions of the Ramachandran plot; 94% of the residues are in favored regions. The somewhat larger than average fraction of residues in generously allowed regions primarily reflects modeling of the 82-90 region in chain B in less well defined electron density.

Accessible surface area calculations were performed with programs based on the Yale algorithm using a probe radius of 1.4 Å. Figures were generated using PyMol.

Molecular Dynamics (MD) Simulations

The preparations and MD simulations were carried out with software implemented in the Schrödinger Suite 2009 (Schrödinger, LCC, New York, N.Y., 2009). Four different systems were built, wild type monomer and trimer, and D105N monomer and trimer mutants, respectively, using the Maestro software, and hydrogens were added using the Protein Preparation Wizard workflow.

Structure of the BRICHOS Domain

Crystals suitable for structure determination were obtained from recombinant CTC subjected to in situ proteolysis with trypsin. The size of the crystallized protein was determined by MS to correspond to an average molecular mass of 11540 Da. Considering the predicted trypsin cleavage sites, this is compatible with a product covering L82-K160 and D168-Y197. The circular dichroism spectrum for trypsin-treated material is essentially the same as for CTC, and both bind the tripeptide VVV, which is a sequence representative of the TM part of proSP-C20. This argues that the trypsin treatment of CTC has not significantly altered the structured part, and that the flexible parts are not crucial for substrate binding.

Figure 7:
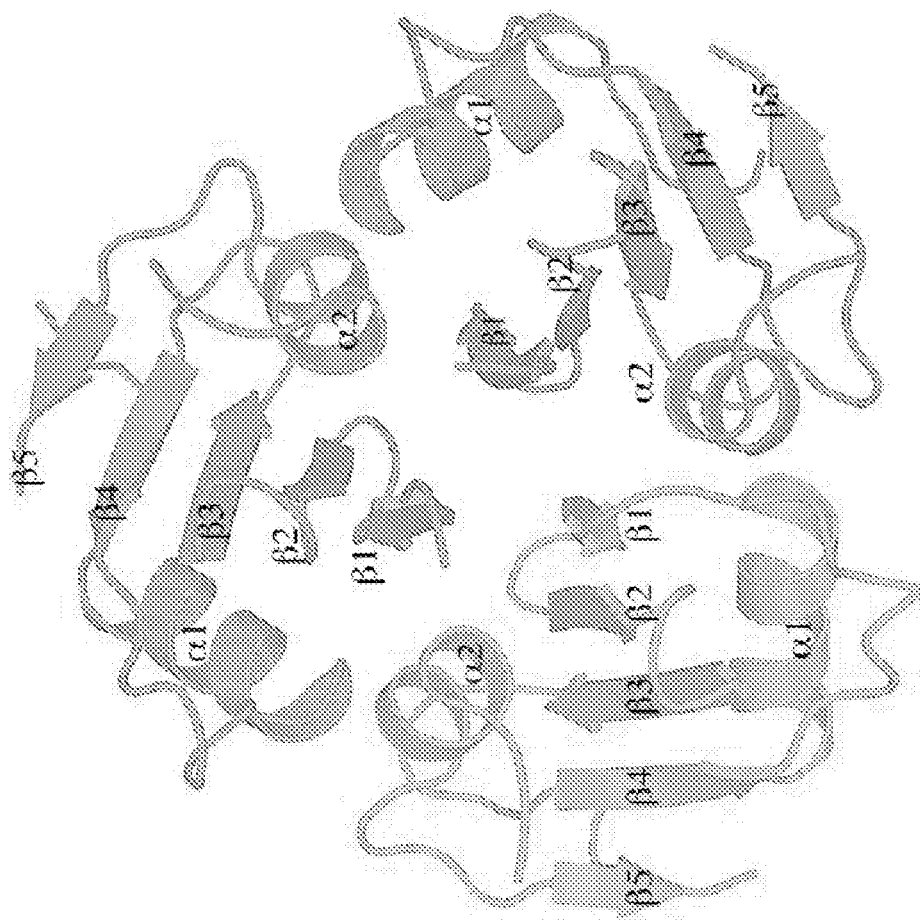
FIG. 7 shows a ribbon diagram showing the organisation of subunits in the proSP-C Brichos trimer.

There are two trimers in the asymmetric unit of the crystals. The structure of the proSP-C BRICHOS trimer is shown in FIG. 7, a ribbon diagram showing the organisation of subunits in the proSP-C BRICHOS trimer. The trimer subunits are arranged to form a trefoil propeller with the β-sheets corresponding to the propeller blades (strand order β1, β2, β3, β4, β5 from the centre to the periphery), and with helices from two subunits on both sides of each propeller blade. The three β1 strands interact closely around the 3-fold axis at the centre of the trimer. Helix α2 of each subunit packs almost head-to-tail with α1 of a neighbouring subunit and also interacts with the two inner strands of the same neighbour.

Figure 6:
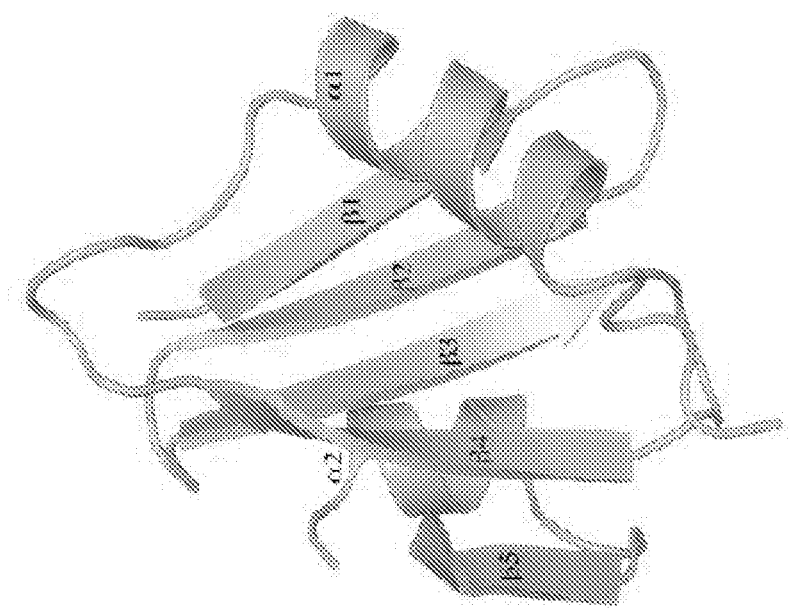
FIG. 6 shows a ribbon diagram representation of one CTC subunit.

No structural homologs are present in the structure database, and the fold of the proSP-C BRICHOS domain has not been observed until now. The domain encompasses residues 90-197 of proSP-C and has an overall architecture where two α-helices enclose a central five-stranded β-sheet. Four consecutive strands in the N-terminal half of the domain form an up-and-down antiparallel β-sheet. The fifth, C-terminal, strand lies parallel to β4, and the two helices following β1-β4 stretch diagonally across each side of the β-sheet. We will use 'face A' to denote the face of the β-sheet that packs against helix 1, and 'face B' for the face packing against helix 2. The two helices are amphiphilic, with the hydrophobic side packing against the β-sheet to contribute to the hydrophobic core, and the second side either mainly solvent accessible (α1) or buried in the interface between subunits (α2). Residues 149-180, corresponding to one of the disordered regions defined by HDX-MS of intact CTC and encompassing the proteolyzed 161-167 segment, have little visible electron density in our maps and have not been modelled. FIG. 6 shows a ribbon diagram representation of one CTC subunit, with secondary structure elements β1-β2-β3-β4-α1-α2-β5 labelled. A dashed line indicates the missing region between helices α1 and α2.

BRICHOS β-Sheet Face A is a Likely Peptide Binding Surface and its Accessibility is Regulated by Strictly Conserved Asp105

ProSP-C is highly conserved across the animal kingdom and particularly among mammals. Conserved residues in the BRICHOS domain of proSP-C were mapped on the crystal structure to identify structurally important positions and potential peptide binding surfaces. A number of conserved Gly and Pro residues located in loop regions may be important for the fold and dynamical properties of the domain. A conserved disulphide bridge between C121 and C189 links β4 and α2 and might be important for stability. The remaining strictly conserved residues are located primarily on face A and B of the β-sheet. Many of the CTC point mutations identified in patients with ILD coincide with strictly conserved amino acid sites.

Many of the hydrophobic core residues in the β-sheet (in particular on face A) are strictly conserved, while helix residues in the hydrophobic core show a wider distribution of hydrophobic side chains, as expected for such positions. This suggests that the β-sheet side chains are conserved not because they are strictly required for formation of the hydrophobic core, but because they are involved in some other function, such as peptide binding. This would, however, require substantial reorganisation of the structure to expose one or both of the β-sheet faces to solution and allow binding.

The aspartic acid residue at position 105 of proSP-C is the only strictly conserved non-disulphide residue in all known BRICHOS sequences, and two mutations of D105 are known to associate with ILD. It is the first residue in a stretch of four conserved residues at the end of beta strand β2 and beginning of strand β3. The side chain is located in a partially hydrophobic surrounding and is in contact with the N-terminal end of α2. We investigated the possibility of a structural role for Asp105 by carrying out MD simulations both on the monomer from the crystal structure (wt) and the monomer with a D105N substitution (D105N). The MD simulations were performed at successively higher temperatures in order to monitor structural stability. Monomeric wt and D105N behave very differently in the simulations. Whereas there are only minor conformational changes in the mutant, several larger scale changes occur in wt at moderately elevated temperatures. The N-terminal part of α2 unwinds and this region communicates via the β-sheet with α1 and the connecting loop from strand β4, which undergo a conformational change that moves helix 1 out from face A by 5-7 Å. This repositioning is accompanied by many of the hydrophobic core residues on face A becoming solvent accessible. More than 500 Å$^2$ hydrophobic surface area on face A is exposed when α1 moves away from the sheet. Hence, the strictly conserved Asp side chain appears to tune the stability of the structure, thereby providing a mechanism for exposing the central β-sheet, and in particular the highly conserved face A, which would make it accessible for binding to e.g. peptide substrates.

Steric Chaperone Function of the BRICHOS Domain

Data on binding of CTC to SP-C in phospholipid membranes show that unstructured, synthetic non-helical forms of SP-C are recognized and converted to helical structure whereas helical SP-C is not recognized. This suggests that CTC acts as a steric chaperone for the extremely hydrophobic and β-structure prone TM proSP-C peptide segment, and that it specifically captures non-native proSP-C in the aforementioned β-hairpin structure. The conserved hydrophobic surfaces of the central β-sheet appear well suited for such a function. In several ways this would parallel how other steric chaperones work. One example would be the steric chaperones of the chaperone/usher pathway where a hydrophobic platform is used to capture unfolded structures and promote their folding to a specific structure, by acting as a folding template/scaffold. Chaperones more or less invariably utilize some sort of "capping" mechanism to shield their hydrophobic binding surfaces from solution in the absence of substrate, often by forming homo-complexes that bury these surfaces. MD simulations using both the crystallographic wt and D105N mutant trimer model as starting structures show that none of the movements that occur in the wt monomeric structure can occur in the trimer. The trimer thus stabilizes the subunit in a conformation that blocks the putative binding site, consistent with its role as a chaperone capping mechanism. Notably, the Δ91-93 deletion mutant and many of the point mutations are situated in the BRICHOS trimer interface.

It was recently shown that for the amyloid β-peptide (Aβ) associated with Alzheimer's disease, a strand-loop-strand structure is required for formation of cytotoxic oligomers and fibrils. Together with the observations that proSP-C and Bri2 BRICHOS domains prevent fibril formation of Aβ and medin, associated with aortic amyloid, this suggest that BRICHOS binds a common intermediate motif in amyloid formation. Our study provides an important stepping-stone for further understanding of a chaperone domain that might be harnessed in therapeutic strategies against amyloid disease.

Example 4

Aggregation Kinetics for Aβ Peptides

Peptides and Proteins
  Aβ Peptides.
  Aβ(M1-40) (SEQ ID NO: 10) and Aβ(M1-42) (SEQ ID NO: 11) were expressed in *E. coli* from synthetic genes and purified in batch format using ion exchange and size exclusion steps, which results in highly pure monomeric peptide. Purified peptide was divided into 20-30 identical aliquots and frozen. Monomer was then isolated by gel filtration of an aliquot of purified peptide just prior to setting up each of the experiments to remove traces of aggregate formed during freezing and thawing and to exchange buffer to the one used in the respective experiment. The latter part of the monomer peak was collected in low-bind Eppendorf tubes (Axygene) on ice and the concentration was determined by absorbance and amino acid analysis after acid hydrolysis. The monomer was used as is or diluted to the desired concentration for the respective experiment.
  Bri2 BRICHOS.
  The expression and purification of the Bri2 BRICHOS domain have been described previously (Peng et al., Biochem. Biophys. Res. Commun., 393: 356-361 (2010)). Briefly, the Bri2 BRICHOS construct was expressed in *E. coli* as a fusion protein with thioredoxin/His$_6$/and S-tag. The protein was then purified using two rounds of Ni-NTA agarose column chromatography. Thrombin was used to remove the thioredoxin- and His$_6$-tag. The eluted protein was analysed with SDS-PAGE and non-denaturing PAGE. The concentration was determined by amino acid analysis after acid hydrolysis.
  ProSP-C BRICHOS.
  A region from nucleotide 175 (His59) to nucleotide 591 (Ile197) of the proSP-C cDNA sequence was amplified from FirstChoice PCR-Ready human lung cDNA (Ambion, Cambridgeshire, UK). For expression, *E. coli* strain Origami B (DE3) pLysS (Novagen, Madison, Wis.) was grown at 30° C. in LB medium with 100 μg/ml ampicillin. Expression was induced at an OD$_{600}$ around 1.2 by 0.5 mM isopropyl β-D-thiogalactopyrano-side (IPTG), and the bacteria were grown for another 4 h at 25° C. The cells were harvested by centrifugation at 6000 g for 15 min at 4° C., and the pellets were resuspended in 20 mM Tris pH 8 and stored at −20° C. The cells were lysed by lysozyme (1 mg/ml) for 30 minutes and incubated with DNase and 2 mM MgCl$_2$ for 30 min on ice. The cell lysate was centrifuged at 6000 g for 20 min and the pellet was suspended in 2 M urea in 20 mM Tris, 0.1 M NaCl, pH 8 and sonicated for 5 min. After centrifugation at 6000 g for 30 min at 4° C., the supernatant was filtered through a 5 μm filter and poured on a 2.5 ml Ni-Agarose column (Qiagen, Ltd., West Sussex, UK). The column was washed with 100 ml 2 M urea in 20 mM Tris, 0.1 M NaCl, pH 8 and then with 100 ml 1 M urea in 20 mM Tris, 0.1 M NaCl, pH 8, and finally with 100 ml 20 mM Tris, 0.1 M NaCl, 20 mM imidazole, pH 8. The protein was eluted with 200 mM imidazole in 20 mM Tris, 0.1 M NaCl, pH 8, and dialyzed against 20 mM Tris, 0.05 M NaCl, pH 8, and cleaved by thrombin for 16 h at 4° C. (enzyme/substrate weight ratio of 0.002) to remove the thioredoxin and His$_6$-tag, and then reapplied to a Ni$^{2+}$ column to remove the released tag. After elution from the Ni$^{2+}$ column, the protein was applied to an anion exchange column (HiTrap QFF, Amersham Biosciences) equilibrated with 20 mM Tris, 20 mM NaCl pH 7.4, eluted as a single peak using a linear gradient from 20 mM to 1 M NaCl, and finally dialyzed against 20 mM Tris, pH 7.4. The concentration was determined by amino acid analysis after acid hydrolysis.

The amino acid sequences of Bri2 Brichos and proSP-C Brichos are presented in FIG. 8. The alignment of proSP-C and Bri2 Brichos domains is made with Clustal W and corresponds to the proSP-C domain as derived from the x-ray structure. Asterisks and double dots mark identical residues and conservative replacements, respectively.

Anti-Thrombin.
  Human anti-thrombin was purchased from Baxter (Vienna, Austria).
  Cystatin C.
  Chicken cystatin C was purified from egg white.
  Monellin.
  Single-chain monellin with net charge −2 (scMN-2; obtained through mutagenesis to incorporate the five substitutions C41S, Q13E, N14D, Q28E, and N50D) was expressed in *E. coli* from a synthetic gene and purified using ion exchange and size exclusion chromatography.

Aggregation Kinetics
  Aggregation kinetics were studied by recording the ThT fluorescence intensity as a function of time in a plate reader (FluoStar Omega from BMG Labtech, Offenberg, Germany). The fluorescence was recorded using bottom optics in half-area 96-well PEG-coated black polystyrene plates with clear bottom (Corning 3881) using a 440 nm excitation filter and a 480 nm emission filter. Aβ monomer was isolated by gel filtration as above in 20 mM Na-phosphate, 200 μM EDTA, 0.02% NaN$_3$ (at pH 7.4 in the case of Aβ(M1-40) and at pH 8.0 for Aβ(M1-42)) and diluted to 6 or 8 μM in the case of Aβ(M1-40) and 3 or 6 μM in the case of Aβ(M1-42) in the same buffer and supplemented with 20 μM ThT from a 2 mM stock. To each well in the 96-well plate was first added either 10 μl buffer (20 mM Tris/HCl pH 7.4) or 10 μl of BRICHOS protein or control protein at ten times the desired final concentration in 20 mM Tris/HCl pH 7.4. To each well was then added 90 μl of the ice-cold Aβ monomer solution and the plate was immediately placed in the plate reader at 37° C., with fluorescence read every 6 minutes with continuous shaking at 100 rpm between readings. Aβ(M1-40) was studied alone or with proSP-C BRICHOS at concentrations ranging from 17 nM to 17 μM or Bri2 BRICHOS at concentration ranging from 60 nM to 6 μM. Aβ(M1-42) was studied alone or with proSP-C BRICHOS at concentrations ranging from 60 μM to 17 μM or Bri2 BRICHOS at concentration ranging from 20 nM to 6 μM. The concentrations of Aβ and BRICHOS proteins were determined by amino acid analysis after acid hydrolysis.

The half time $t_{1/2}$ was obtained by fitting a sigmoidal function to each kinetic trace $$y=y_0+(y_{max}-y_0)/(1+\exp(-k(t-t_{1/2})))$$

and the lag time, $t_{lag}$ was defined as $$t_{lag}=t_{1/2}-2/k.$$

Thioflavin T (ThT) was used as a reporter on fibril formation in kinetic experiments for Aβ(M1-40) or Aβ(M1-42), herein referred to as Aβ40 and Aβ42, respectively, alone or with different concentrations of the BRICHOS proteins ranging from 0.00001 to 0.6 molar equivalents.

Examples of aggregation kinetics for Aβ40 alone and with 0.018 or 0.18 molar equivalents of proSP-C BRICHOS are shown in FIG. 9A, and with 0.017 and 0.061 molar equivalents of Bri2 BRICHOS in FIG. 9B. The mid-point of the aggregation process, $t_{1/2}$ and the lag time were obtained from each kinetic trace by fitting a sigmoidal function to the data. The values of $t_{1/2}$ relative to that of the undisturbed case are plotted versus molar ratio of BRICHOS:Aβ40 in FIG. 9C where each data point and error bar represents the average and standard deviation based on six to eight replicates. Clearly, the lag time for Aβ40 aggregation has increased extensively in the presence of proSP-C or Bri2 BRICHOS, while the elongation rate is largely unaffected. Very large effects on the lag time are observed far below equimolar concentration of proSP-C or Bri2 BRICHOS relative to Aβ40. A doubling of the lag time for Aβ40 aggregation requires ca. 0.01 molar equivalents of proSP-C BRICHOS, and a 10-fold increase in lag time is seen around 0.01 equivalents of Bri2 BRICHOS or 0.03 equivalents of proSP-C BRICHOS. The retarding effect increases with increasing BRICHOS concentration, and the lag time exceeds one week and becomes practically difficult to quantify above 0.025 (1 Bri2 BRICHOS per 40 Aβ40)) or 0.06 molar ratio (1 proSP-C BRICHOS per 16 Aβ molecules). Thus both BRICHOS proteins are very potent inhibitors of Aβ40 aggregation, with the strongest effects observed for Bri2 BRICHOS.

Examples of kinetic traces by ThT fluorescence for Aβ42 alone and with 0.10 and 0.62 molar equivalents of proSP-C BRICHOS are shown in FIG. 9D, and with 0.10 and 0.61 molar equivalents of Bri2 BRICHOS in FIG. 9E. The mid-point of the aggregation process, $t_{1/2}$, and error bars based on six to eight replicates at each condition are shown in FIG. 9F. Also for Aβ42, both proSP-C and Bri2 BRICHOS retard the aggregation significantly and only sub-stoichiometric amounts of the BRICHOS proteins are required. At 0.06-0.1 molar ratio (1 BRICHOS protein per 10-16 Aβ42), both the lag time and half time are doubled compared to the uninhibited case, thus the elongation rate is not affected. A ten-fold increase in lag time is seen at ca. 0.6 molar equivalents of the BRICHOS proteins, under which conditions the elongation rate is found to be significantly reduced. Although strong effects are seen on Aβ42 aggregation kinetics, it is clear that higher concentrations of the BRICHOS proteins are needed to exert the same effect as on Aβ40 aggregation, and the retarding effects of proSP-C and Bri2 BRICHOS are quantitatively more similar in the case of Aβ42.

Control experiments were set up to study the aggregation kinetics of Aβ40 and Aβ42 in the presence of the three proteins human anti-thrombin (HAT), egg white cystatin C and a single chain monellin variant (scMN-2). HAT was chosen since it belongs to the serpin family, several members of which have been reported to possess anti-amyloid properties. Egg white cystatin C has about the same molecular mass as the BRICHOS domain, and scMN-2 was chosen because it has the same net charge (−2) as proSP-C BRICHOS, to mimic any non-specific protein effect. Each control protein was added at 0.01 and 0.1 molar equivalents to Aβ40, or to Aβ42, and aggregation followed by the ThT assay. HAT and scMN-2 were found to inhibit aggregation of Aβ40, but required 0.01 and 0.1 molar equivalents, respectively, to produce the same effects as 0.006 molar equivalents of proSP-C BRICHOS or 0.0006 molar equivalents of Bri2 BRICHOS. Thus proSP-C BRICHOS was found to be 10-100-fold more effective inhibitor of Aβ40 aggregation than HAT and scMN-2, and Bri2 BRICHOS 100-1000-fold more effective than these control proteins. HAT also showed effect against Aβ42 when added at 0.1. molar equivalents. No inhibiting effect was observed for cystatin C.

The BRICHOS domains from two human proteins, Bri2 and proSP-C, can prevent Aβ fibril formation in a concentration-dependent manner. The aggregation of the more disease-relevant Aβ42 is retarded at sub-stoichiometric BRICHOS:Aβ42 ratios with a doubling of the aggregation lag time observed at 1 BRICHOS domain per 10 Aβ42. This is an important result, which may be harnessed in design of future AD therapy.

Lower BRICHOS concentration is needed to reach the same inhibitory effect on Aβ40 as compared to Aβ42. As little as 1 Bri2 BRICHOS per 400 Aβ40 (or 1 proSP-C BRICHOS per 160 Aβ40 molecules) is needed for doubling of the lag time. Above 1 Bri2 BRICHOS per 40 Aβ40 (or 1 proSP-C BRICHOS per 10 Aβ40 molecules), the aggregation process is so much retarded that it does not occur within the one-week time frame of the experiment as compared to a few hours for Aβ40 alone.

Example 5

Stopping Experiments for Aβ Peptides

Figure 10:
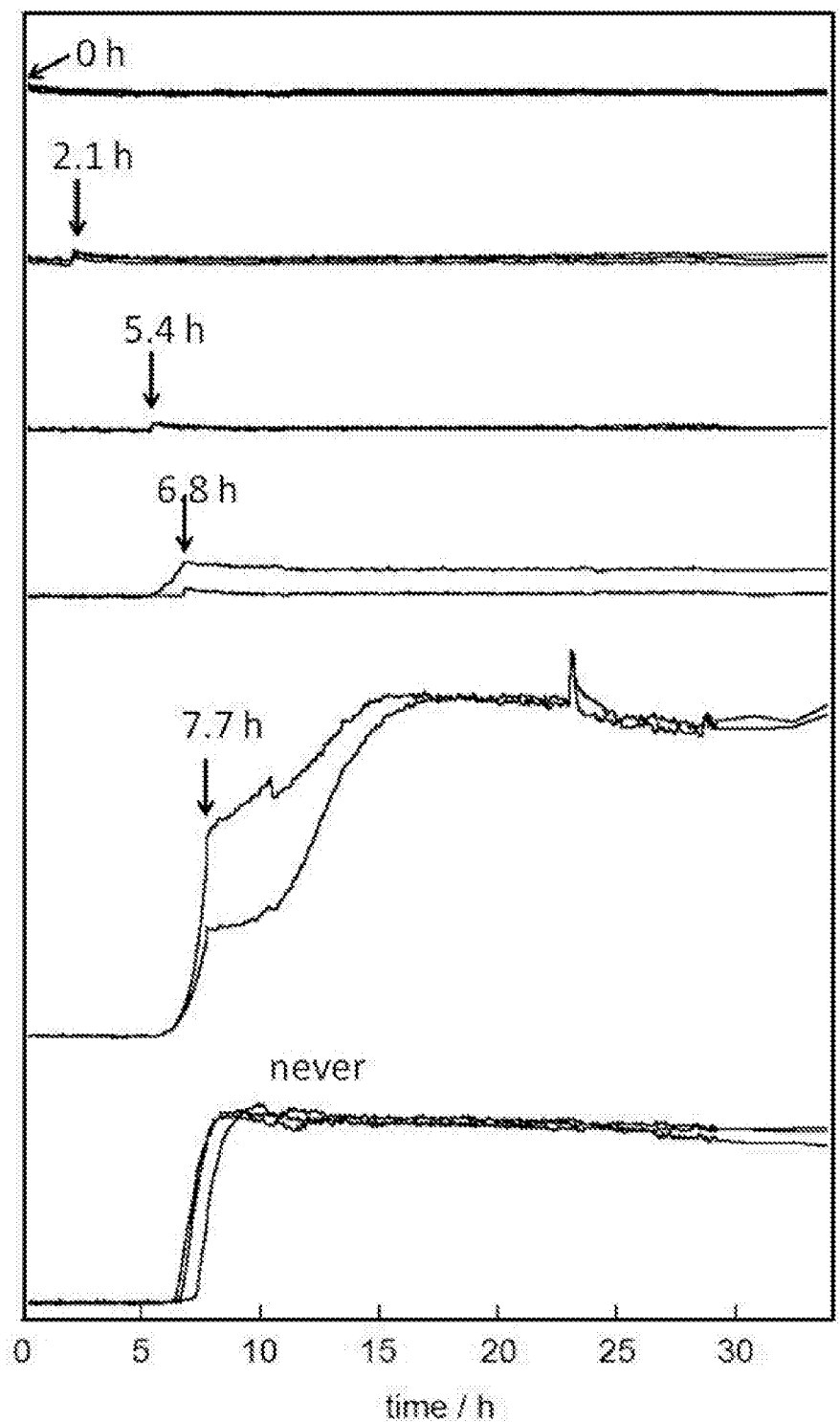
FIG. 10 shows aggregation of 8 µM Aβ40, monitored by recording the ThT fluorescence intensity as a function of time with addition of 800 nM Bri2-BRICHOS at different time points.

To monitor the effect of BRICHOS addition during an ongoing aggregation process, samples with 8 μM Aβ40 were monitored by recording the ThT fluorescence intensity as a function of time. 800 nM Bri2 BRICHOS was added from a concentrated stock just before the start of the experiment, or at different time points ranging from 0.3 to 11.2 hours. A similar experiment was performed for 3 μM Aβ42 with 1.8 μM Bri2 BRICHOS added at different time points ranging from 6 to 109 minutes. As shown in FIG. 10, the aggregation process can be delayed by BRICHOS protein if added anywhere during the lag time. In FIG. 10, aggregation of 8 μM Aβ40 was monitored by recording the ThT fluorescence intensity as a function of time in 20 mM Na-phosphate, pH 7.4, 200 μM EDTA, 20 μM ThT 0.02% NaN$_3$, 37° C. with 100 rpm shaking. 800 nM Bri2 BRICHOS was added from a concentrated stock before the start of the experiment (top traces) or at different time points after starting the experiment (ranging from 0.3 to 11.2 hours) as indicated at the vertical arrows.

If BRICHOS protein is added during the early part of the elongation phase, the process appears to halt with no further growth of the ThT positive aggregates. When added close to the mid-point of the transition, the BRICHOS protein seems to halt the process from further progression or cause the process to reduce its speed and progress at lower rate. When added at the end of the transition, no effect is seen.

The prolonged lag phase and essentially unaffected elongation rate in our kinetic ThT experiments (c.f. Example 4) imply that the BRICHOS proteins mainly disturb processes that occur during the lag phase. This is further illustrated by the results of these stopping experiments where BRICHOS is added during an ongoing aggregation process. We find that fibrillation can be strongly delayed as long as the BRICHOS domains are added during the lag phase. The process is only temporarily halted if BRICHOS is added at the mid-point of the elongation process, and after that it is too late to interfere. These results imply that BRICHOS domains interfere with molecular events that occur during the lag phase.

Example 6

Impact of the Brichos Proteins on the Secondary Structure of Aβ Peptides

CD Spectroscopy

CD spectra were recorded in a 4 mm quartz cuvette using a JASCO J-815 spectropolarimeter. Far-UV spectra were recorded at 1 nm intervals between 185 and 250 nm using a scan rate of 20 nm/min, with response time 8 s, and band pass 1 nm. Aβ(M1-40) monomer was isolated by gel filtration in 10 mM sodium phosphate buffer, pH 7.4 with 40 mM NaF and 200 µM EDTA, collected on ice and divided into three samples which were supplemented with buffer, proSP-C or Bri2 BRICHOS to final concentrations of 8 µM Aβ(M1-40) and no addition or 0.8 µM proSP-C BRICHOS or 0.8 µM Bri2 BRICHOS. The samples were heated to 37° C. and studied directly or after different times of incubation at 37° C. with 100 rpm shaking, up to 18 hours. A spectrum of the buffer was recorded separately in the same cuvette and subtracted from all spectra. Spectra of 0.8 µM proSP-C or Bri2 BRICHOS were recorded separately.

Structural transitions during the aggregation process were studied using CD spectroscopy (data not shown). The data for Aβ40 alone agrees with other reports, and shows a continuous progression from a spectrum typical for random-coil peptide towards a spectrum indicative of β-sheet structure. The structural transition starts to develop while the aggregation process as observed by ThT fluorescence is still in the lag phase and thus reports on the appearance of intermediates with β-sheet structure before fibrillar aggregates can be detected by ThT fluorescence. In the presence of 0.1 molar equivalents of proSP-C BRICHOS or 0.1 molar equivalents of Bri2 BRICHOS, the structural transition appears to be delayed as judged from the spectra at 200 min and 18 h. The spectra at both these time points report on mainly random coil structure and thus imply that the presence of BRICHOS proteins reduces the concentration of intermediates with β-sheet structure and keeps Aβ in a mainly unstructured state during the extended lag phase. The spectrum for Aβ40 plus proSP-C BRICHOS at 18 h has started to convert towards β-structure, indicating that the 18 hour spectrum is taken near the end of the lag phase.

Example 7

Interaction Between the Brichos Proteins and Aβ Peptides

Size Exclusion Chromatography

Size exclusion chromatography on a Superdex75 column (GE Healthcare, Uppsala, Sweden) was performed using a BioLogic HR FPLC system (Biorad). The column was equilibrated and operated in degassed buffer (20 mM Na-phosphate, 200 µM EDTA, 0.02% $NaN_3$ at pH 7.4 or pH 8.0 to prepare samples for aggregation studies, and 10 mM Na-phosphate, 40 mM NaF, pH 7.4, to prepare samples for CD studies). Samples were injected from a 1 mL loop and chromatograms recorded by monitoring the absorbance at 280 nm. To monitor protein interactions, mixtures of Aβ and BRICHOS domains were injected directly after mixing or after 2 or 20 hours incubation at 37° C. in 20 mM Na-phosphate, 200 µM EDTA, 0.02% $NaN_3$ at pH 7.4 or pH 8.0. Fractions (0.3-0.7 ml) were collected during the chromatogram, lyophilized and analyzed by SDS PAGE in a 10-20% gradient gel.

The interaction between the BRICHOS proteins and Aβ was studied using gel filtration. Samples of 8 µM Aβ40 and 0.8 µM proSP-C BRICHOS, or 8 µM Aβ40 and 0.8 µM Bri2 BRICHOS, were incubated for 20 hours at 37° C., followed by gel filtration on a Superdex75 column, and SDS PAGE analysis of collected fractions.

FIG. 11 shows gel filtration of a mixture of 8 µM Aβ40 and 0.8 µM proSP-C BRICHOS, immediately after mixing (top chromatogram) and after 20 hours incubation (bottom) with collected fractions indicated by vertical lines and numbers. A chromatogram of 8 µM Aβ40 alone at 0 h is also shown (this chromatogram was scaled by a factor of 0.5 because twice the volume was injected).

FIG. 12A shows gel filtration on a Superdex 75 column of mixtures 8 µM Aβ40 and 0.8 µM ProSP-C BRICHOS immediately after mixing and after 20 hours incubation (500 µL injected). Absorbance was measured in a 5 mm cell. SDS PAGE of collected, lyophilized and resuspended fractions (10-20% gradient gels) are shown below the chromatograms.

Figure 12B:
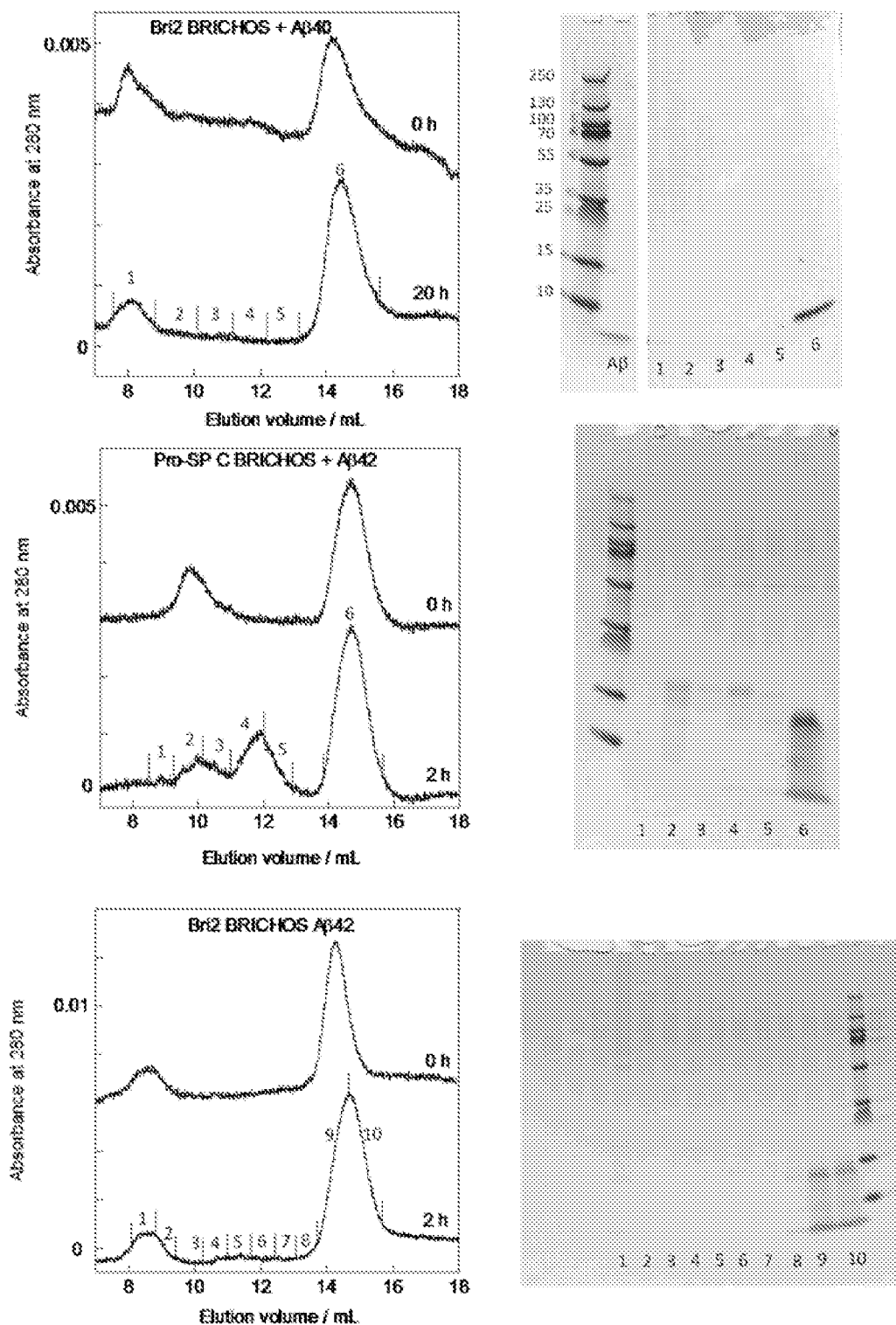
FIG. 12 shows gel filtration of mixtures of Aβ40 or Aβ42, respectively, and proSP-C BRICHOS or Bri2 BRICHOS, respectively, immediately after mixing and after 20 hours incubation. SDS PAGE gels of collected fractions are shown next to the chromatograms.

FIG. 12B shows gel filtration on a Superdex 75 column of mixtures 8 µM Aβ40 and 0.8 µM Bri2 BRICHOS (top), 8 µM Aβ42 and 0.8 µM proSP-C BRICHOS (middle), or 8 µM Aβ42 and 0.8 µM Bri2 BRICHOS (bottom) immediately after mixing and after 2 or 20 hours incubation (250 or 500 µL injected). SDS PAGE of collected, lyophylized and resuspended fractions (10-20% gradient gels) are shown to the right. The band close to the 15 kDa marker is an SDS artifact often seen for Aβ42.

Figure 9:
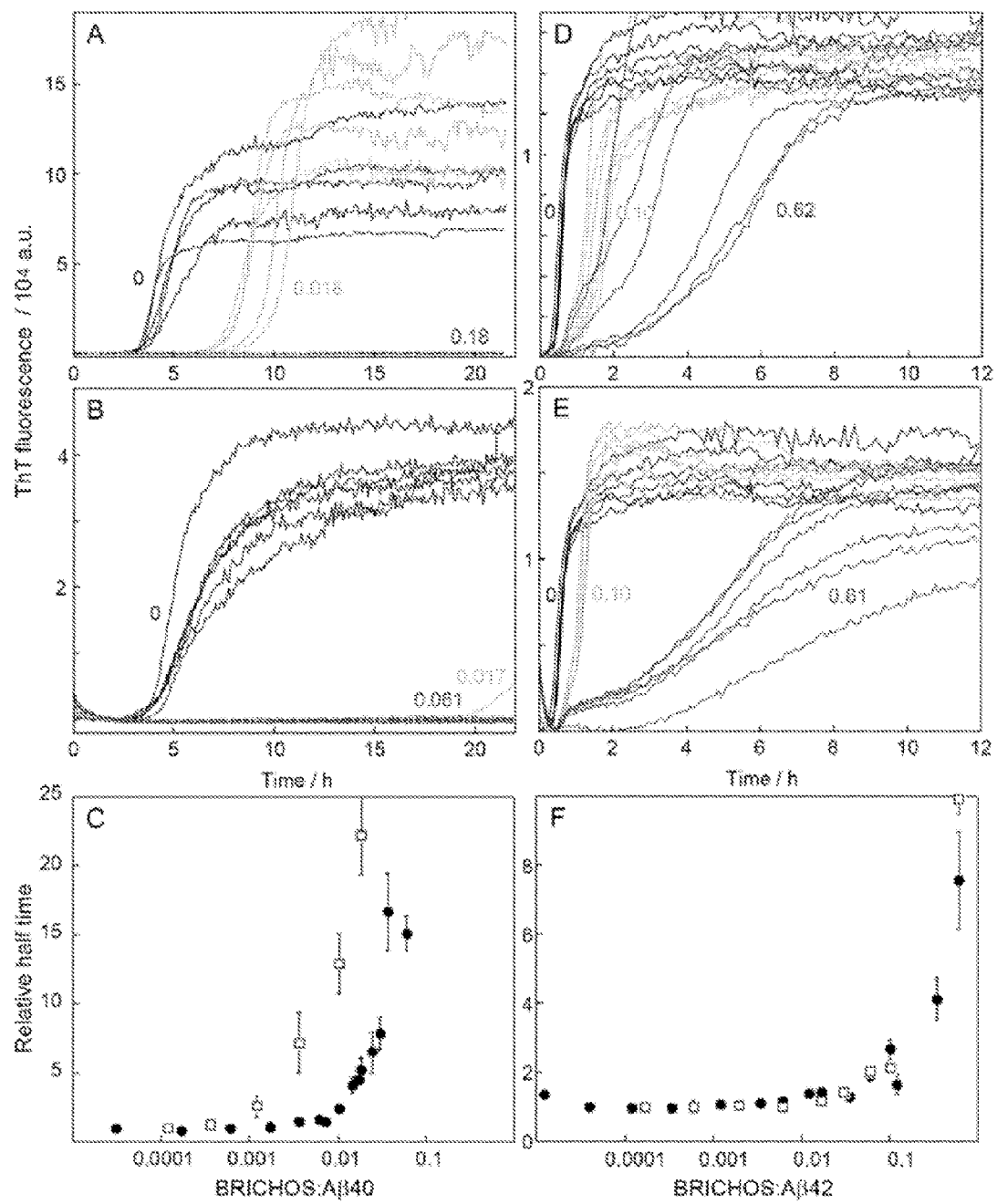
FIG. 9 shows aggregation, monitored by recording the ThT fluorescence intensity, of Aβ40 and Aβ42, respectively, alone and with proSP-C BRICHOS and Bri2 BRICHOS, respectively.

The 20 h time point was chosen for investigating potential interactions between the BRICHOS protein and Aβ, because at this time point Aβ alone would have fibrillated and reached the equilibrium plateau, whereas samples containing 0.1 molar equivalent of proSP-C or Bri2 BRICHOS are still in the lag phase (c.f. FIG. 9). The data in FIG. 11 show clearly that at this time point almost all of Aβ40 is monomeric, while a minor fraction elutes together with proSP-C BRICHOS in fractions 2-6. Similar results are observed for 8 µM Aβ40 and 0.8 µM Bri2 BRICHOS (FIG. 12B). After 20 h, a minor amount of Aβ elutes together with Bri2 BRICHOS, but the majority of Aβ40 is still monomeric, indicating that Bri2 BRICHOS destabilizes oligomeric intermediates and/or inhibits their formation. The observation of small amounts of Aβ40 also in the BRICHOS peak, and in intermediate peaks, plus the finding in some repeats of a skewed Aβ40 monomer peak, indicates that the interactions with BRICHOS proteins occur with exchange rates in the intermediate regime on the gel filtration time scale, i.e. with a dissociation rate constant on the order of 0.001-0.01 $s^{-1}$. Data for 8 µM Aβ42 and 0.8 µM Bri2 BRICHOS or proSP-C BRICHOS at 0 and 2 h incubation (FIG. 12) agree with these findings. The data in FIG. 12A further indicate the presence of a BRICHOS trimer at 0 h, while Aβ peptides (fractions 5-6) elute together with BRICHOS monomers after 20 h.

Example 8

Aβ Kinetics with Ligands Experiments

Experiments were performed to determine if addition of candidate compounds that supposedly decrease the trimer/monomer ratio to recombinant human proSP-C BRICHOS or to recombinant human Bri2 BRICHOS can increase the efficacy of the BRICHOS domains as regards inhibition of Aβ fibril formation.

Aβ Peptide Preparation

Aβ(M1-40) and Aβ(M1-42) were expressed in *E. coli* from synthetic genes and purified in batch format using ion exchange and size exclusion steps as described.

Aggregation Kinetics

Aggregation kinetics were studied by recording the Thioflavin T (ThT) fluorescence intensity as a function of time in a plate reader (FluoStar Omega from BMG Labtech, Offenberg, Germany). The fluorescence was recorded using bottom optics in half-area 96-well PEG-coated black polystyrene plates with clear bottom (Corning 3881) using 440 nm excitation filter and 480 nm emission filter.

Each sample (100 μl) containing 6 μM Aβ(M1-40) in 20 mM Na-phosphate, 200 μM EDTA, 0.02% NaN3 at pH 7.4 and 20 μM ThT, was prepared with 120 nM proSP-C BRICHOS or 30 nM Bri2 BRICHOS protein, pre-incubated for 30 min with 1:1 or 1:10 molar ratio of acetyl-YYY-amide peptide, VVV peptide or bis-ANS (1,1'-bis(4-anilino-5,5'-naphthalenesulfonate)). Thus, for proSP-C BRICHOS 120 nM or 1.2 μM tripeptide or bis-ANS were used, and for Bri2 BRICHOS 30 nM or 300 nM of tripeptide or bis-ANS were used.

Aβ(M1-40) fibril formation was studied alone or in the presence of proSP-C or Bri2 BRICHOS, with or without tri-peptide or bis-ANS. The 96-well plate was, immediately after mixing the samples, placed in the plate reader at 37° C., with fluorescence read every 6 minutes with continuous shaking at 100 rpm between readings.

Results

Recombinant human proSP-C or Bri2 BRICHOS alone delayed the onset of Aβ fibril formation, i.e. prolonged the lag phase. Addition of 120 nM bis-ANS to proSP-C BRICHOS, or addition of 300 nM bis-ANS to Bri2 BRICHOS, significantly potentiated the delay in onset of fibril formation. For proSP-C BRICHOS, addition of 120 nM bis-ANS approximately doubled the lag time, while addition of 300 nM bis-ANS to Bri2 BRICHOS prolonged the lag time at least three-fold. Addition of the tripeptides had no detectable effect on the ability of the BRICHOS domains to delay Aβ fibril formation.

These experiments indicate that addition of specific ligands to human proSP-C or Bri2 BRICHOS-containing proteins can potentiate their ability to retard Aβ fibril formation, and that such ligands can be screened for using the approach described here.

The invention claimed is:

1. A method of screening a candidate compound for activity in activating a chaperon protein that decreases the fibril formation of Aβ-peptide, the method comprising determining whether the trimer/monomer ratio of a chaperone protein decreases in the presence of the candidate compound, wherein a decrease in the trimer/monomer ratio is associated with activity in activating the chaperon protein that decreases the fibril formation, wherein the chaperon protein comprises the amino acid sequence selected from the group consisting of SEQ ID NO:3 and residues 90-243 of integral membrane protein 2B (Bri2) from human (SEQ ID NO: 2), wherein determining whether the trimer/monomer ratio of a chaperone protein is decreased comprises the steps of:
   a) adding the candidate compound to an aqueous mixture comprising a known trimer/monomer ratio of the chaperone protein;
   b) allowing the candidate compound to interact with the chaperone protein in the mixture;
   c) determining the trimer/monomer ratio of the chaperone protein in the mixture;
   d) concluding that the candidate compound is
   d1) active in activating the chaperone protein if the trimer/monomer ratio of the chaperone protein is decreased in the presence of the candidate compound; or
   d2) not active in activating the chaperone protein if the trimer/monomer ratio of the chaperone protein is not decreased in the presence of the candidate compound.

2. The method according to claim 1, wherein the chaperone protein comprises less than or equal to 200 amino acid residues.

3. A method of screening one or more candidate compound(s) for activity in decreasing the aggregation or fibril formation of $A\beta_{1-40}$ and/or $A\beta_{1-42}$ peptides, wherein the aggregation or the fibril formation is retarded by $Bri2_{Brichos}$ monomers, the method comprising determining whether the trimer/monomer ratio of a chaperone protein is decreased in the presence of said one or more candidate compound(s), wherein the chaperone protein comprises the amino acid sequence selected from the group consisting of residues 90-243 of integral membrane protein 2B (Bri2) from human (SEQ ID NO: 2) and the Brichos domain of Bri2 from human (SEQ ID NO: 3), wherein determining whether the trimer/monomer ratio of a chaperone protein is decreased comprises the steps of:
   a) adding said one or more candidate compound(s) to an aqueous mixture comprising a known trimer/monomer ratio of the chaperone protein;
   b) allowing said one or more candidate compound(s) to interact with the chaperone protein in the mixture; and
   c) determining the trimer/monomer ratio of the chaperone protein in the mixture;
   d) concluding that said one or more candidate compound(s) is
   d1) active in decreasing the aggregation or fibril formation of $A\beta_{1-40}$ and/or $A\beta_{1-42}$ peptides if the trimer/monomer ratio of the chaperone protein is decreased in the presence of the candidate compound(s); or
   d2) not active in decreasing the aggregation or fibril formation of $A\beta_{1-40}$ and/or $A\beta_{1-42}$ peptides if the trimer/monomer ratio of the chaperone protein is not decreased in the presence of the candidate compound(s).

4. The method according to claim 3, wherein the chaperone protein comprises less than or equal to 200 amino acid residues.

5. The method according to claim 3, further comprising determining whether the formation of fibrils of $A\beta$-peptide is decreased in the presence of the chaperone protein and the candidate compound(s), comprising the steps of:
   e) providing a second aqueous mixture comprising the $A\beta$-peptide and the chaperone protein;
   f) adding the candidate compound(s) considered active in step d1) to the second mixture to decrease the trimer/monomer ratio of the chaperone protein;
   g) allowing the chaperone protein to interact with the candidate compound(s) and with the $A\beta$-peptide in the second mixture; and
   h) determining the formation of fibrils of the $A\beta$-peptide in the second mixture.

* * * * *

SEQUENCE LISTING

```
<160> NUMBER OF SEQ ID NOS: 14

<210> SEQ ID NO 1
<211> LENGTH: 266
<212> TYPE: PRT
<213> ORGANISM: Homo sapiens

<400> SEQUENCE: 1

Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
            85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Phe Glu Glu Glu Val Glu
        115                 120                 125

Phe Ile Ser Val Pro Val Pro Glu Phe Ala Asp Ser Asp Pro Ala Asn
        130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175
```

-continued

Pro Arg Asn Leu Leu Glu Leu Ile Asn Ile Lys Ala Gly Thr Tyr
            180                 185                 190

Leu Pro Gln Ser Tyr Leu Ile His Glu His Met Val Ile Thr Asp Arg
            195                 200                 205

Ile Glu Asn Ile Asp His Leu Gly Phe Phe Ile Tyr Arg Leu Cys His
210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                    245                 250                 255

Lys Phe Ala Val Glu Thr Leu Ile Cys Ser
            260                 265

<210> SEQ ID NO 2
<211> LENGTH: 154
<212> TYPE: PRT
<213> ORGANISM: Homo sapiens

<400> SEQUENCE: 2

Gly Ile Lys Tyr Ile Lys Asp Asp Val Ile Leu Asn Glu Pro Ser Ala
1               5                   10                  15

Asp Ala Pro Ala Ala Leu Tyr Gln Thr Ile Glu Glu Asn Ile Lys Ile
            20                  25                  30

Phe Glu Glu Glu Val Glu Phe Ile Ser Val Pro Val Pro Glu Phe
            35                  40                  45

Ala Asp Ser Asp Pro Ala Asn Ile Val His Asp Phe Asn Lys Lys Leu
50                  55                  60

Thr Ala Tyr Leu Asp Leu Asn Leu Asp Lys Cys Tyr Val Ile Pro Leu
65                  70                  75                  80

Asn Thr Ser Ile Val Met Pro Pro Arg Asn Leu Leu Glu Leu Leu Ile
                85                  90                  95

Asn Ile Lys Ala Gly Thr Tyr Leu Pro Gln Ser Tyr Leu Ile His Glu
            100                 105                 110

His Met Val Ile Thr Asp Arg Ile Glu Asn Ile Asp His Leu Gly Phe
            115                 120                 125

Phe Ile Tyr Arg Leu Cys His Asp Lys Glu Thr Tyr Lys Leu Gln Arg
        130                 135                 140

Arg Glu Thr Ile Lys Gly Ile Gln Lys Arg
145                 150

<210> SEQ ID NO 3
<211> LENGTH: 95
<212> TYPE: PRT
<213> ORGANISM: Homo sapiens

<400> SEQUENCE: 3

Phe Ala Asp Ser Asp Pro Ala Asn Ile Val His Asp Phe Asn Lys Lys
1               5                   10                  15

Leu Thr Ala Tyr Leu Asp Leu Asn Leu Asp Lys Cys Tyr Val Ile Pro
            20                  25                  30

Leu Asn Thr Ser Ile Val Met Pro Pro Arg Asn Leu Leu Glu Leu Leu
            35                  40                  45

Ile Asn Ile Lys Ala Gly Thr Tyr Leu Pro Gln Ser Tyr Leu Ile His
        50                  55                  60

Glu His Met Val Ile Thr Asp Arg Ile Glu Asn Ile Asp His Leu Gly
65                  70                  75                  80

```
Phe Phe Ile Tyr Arg Leu Cys His Asp Lys Glu Thr Tyr Lys Leu
            85                  90                  95
```

```
<210> SEQ ID NO 4
<211> LENGTH: 267
<212> TYPE: PRT
<213> ORGANISM: Homo sapiens

<400> SEQUENCE: 4

Met Val Lys Ile Ser Phe Gln Pro Ala Val Ala Gly Ile Lys Gly Asp
1               5                   10                  15

Lys Ala Asp Lys Ala Ser Ala Ser Ala Pro Ala Pro Ser Ala Thr
            20                  25                  30

Glu Ile Leu Leu Thr Pro Ala Arg Glu Glu Gln Pro Gln His Arg
            35                  40                  45

Ser Lys Arg Gly Gly Ser Val Gly Gly Val Cys Tyr Leu Ser Met Gly
        50                  55                  60

Met Val Val Leu Leu Met Gly Leu Val Phe Ala Ser Val Tyr Ile Tyr
65                  70                  75                  80

Arg Tyr Phe Phe Leu Ala Gln Leu Ala Arg Asp Asn Phe Phe Arg Cys
                85                  90                  95

Gly Val Leu Tyr Glu Asp Ser Leu Ser Ser Gln Val Arg Thr Gln Met
            100                 105                 110

Glu Leu Glu Glu Asp Val Lys Ile Tyr Leu Asp Glu Asn Tyr Glu Arg
        115                 120                 125

Ile Asn Val Pro Val Pro Gln Phe Gly Gly Gly Asp Pro Ala Asp Ile
130                 135                 140

Ile His Asp Phe Gln Arg Gly Leu Thr Ala Tyr His Asp Ile Ser Leu
145                 150                 155                 160

Asp Lys Cys Tyr Val Ile Glu Leu Asn Thr Thr Ile Val Leu Pro Pro
                165                 170                 175

Arg Asn Phe Trp Glu Leu Leu Met Asn Val Lys Arg Gly Thr Tyr Leu
            180                 185                 190

Pro Gln Thr Tyr Ile Ile Gln Glu Glu Met Val Val Thr Glu His Val
        195                 200                 205

Ser Asp Lys Glu Ala Leu Gly Ser Phe Ile Tyr His Leu Cys Asn Gly
    210                 215                 220

Lys Asp Thr Tyr Arg Leu Arg Arg Arg Ala Thr Arg Arg Ile Asn
225                 230                 235                 240

Lys Arg Gly Ala Lys Asn Cys Asn Ala Ile Arg His Phe Glu Asn Thr
                245                 250                 255

Phe Val Val Glu Thr Leu Ile Cys Gly Val Val
            260                 265
```

```
<210> SEQ ID NO 5
<211> LENGTH: 146
<212> TYPE: PRT
<213> ORGANISM: Homo sapiens

<400> SEQUENCE: 5

Gly Val Leu Tyr Glu Asp Ser Leu Ser Ser Gln Val Arg Thr Gln Met
1               5                   10                  15

Glu Leu Glu Glu Asp Val Lys Ile Tyr Leu Asp Glu Asn Tyr Glu Arg
            20                  25                  30

Ile Asn Val Pro Val Pro Gln Phe Gly Gly Gly Asp Pro Ala Asp Ile
        35                  40                  45
```

```
Ile His Asp Phe Gln Arg Gly Leu Thr Ala Tyr His Asp Ile Ser Leu
    50                  55                  60

Asp Lys Cys Tyr Val Ile Glu Leu Asn Thr Thr Ile Val Leu Pro Pro
 65                  70                  75                  80

Arg Asn Phe Trp Glu Leu Leu Met Asn Val Lys Arg Gly Thr Tyr Leu
                 85                  90                  95

Pro Gln Thr Tyr Ile Ile Gln Glu Glu Met Val Val Thr Glu His Val
                100                 105                 110

Ser Asp Lys Glu Ala Leu Gly Ser Phe Ile Tyr His Leu Cys Asn Gly
            115                 120                 125

Lys Asp Thr Tyr Arg Leu Arg Arg Ala Thr Arg Arg Ile Asn
    130                 135                 140

Lys Arg
145

<210> SEQ ID NO 6
<211> LENGTH: 95
<212> TYPE: PRT
<213> ORGANISM: Homo sapiens

<400> SEQUENCE: 6

Phe Gly Gly Gly Asp Pro Ala Asp Ile Ile His Asp Phe Gln Arg Gly
  1               5                  10                  15

Leu Thr Ala Tyr His Asp Ile Ser Leu Asp Lys Cys Tyr Val Ile Glu
                 20                  25                  30

Leu Asn Thr Thr Ile Val Leu Pro Pro Arg Asn Phe Trp Glu Leu Leu
             35                  40                  45

Met Asn Val Lys Arg Gly Thr Tyr Leu Pro Gln Thr Tyr Ile Ile Gln
         50                  55                  60

Glu Glu Met Val Val Thr Glu His Val Ser Asp Lys Glu Ala Leu Gly
 65                  70                  75                  80

Ser Phe Ile Tyr His Leu Cys Asn Gly Lys Asp Thr Tyr Arg Leu
                 85                  90                  95

<210> SEQ ID NO 7
<211> LENGTH: 197
<212> TYPE: PRT
<213> ORGANISM: Homo sapiens

<400> SEQUENCE: 7

Met Asp Val Gly Ser Lys Glu Val Leu Met Glu Ser Pro Pro Asp Tyr
  1               5                  10                  15

Ser Ala Ala Pro Arg Gly Arg Phe Gly Ile Pro Cys Cys Pro Val His
                 20                  25                  30

Leu Lys Arg Leu Leu Ile Val Val Val Val Val Leu Ile Val Val
             35                  40                  45

Val Ile Val Gly Ala Leu Leu Met Gly Leu His Met Ser Gln Lys His
         50                  55                  60

Thr Glu Met Val Leu Glu Met Ser Ile Gly Ala Pro Glu Ala Gln Gln
 65                  70                  75                  80

Arg Leu Ala Leu Ser Glu His Leu Val Thr Thr Ala Thr Phe Ser Ile
                 85                  90                  95

Gly Ser Thr Gly Leu Val Val Tyr Asp Tyr Gln Gln Leu Leu Ile Ala
                100                 105                 110

Tyr Lys Pro Ala Pro Gly Thr Cys Cys Tyr Ile Met Lys Ile Ala Pro
            115                 120                 125
```

Glu Ser Ile Pro Ser Leu Glu Ala Leu Asn Arg Lys Val His Asn Phe
            130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
                180                 185                 190

Pro Leu Tyr Tyr Ile
            195

<210> SEQ ID NO 8
<211> LENGTH: 139
<212> TYPE: PRT
<213> ORGANISM: Homo sapiens

<400> SEQUENCE: 8

His Met Ser Gln Lys His Thr Glu Met Val Leu Glu Met Ser Ile Gly
1               5                   10                  15

Ala Pro Glu Ala Gln Gln Arg Leu Ala Leu Ser Glu His Leu Val Thr
            20                  25                  30

Thr Ala Thr Phe Ser Ile Gly Ser Thr Gly Leu Val Val Tyr Asp Tyr
        35                  40                  45

Gln Gln Leu Leu Ile Ala Tyr Lys Pro Ala Pro Gly Thr Cys Cys Tyr
    50                  55                  60

Ile Met Lys Ile Ala Pro Glu Ser Ile Pro Ser Leu Glu Ala Leu Asn
65                  70                  75                  80

Arg Lys Val His Asn Phe Gln Met Glu Cys Ser Leu Gln Ala Lys Pro
                85                  90                  95

Ala Val Pro Thr Ser Lys Leu Gly Gln Ala Glu Gly Arg Asp Ala Gly
            100                 105                 110

Ser Ala Pro Ser Gly Gly Asp Pro Ala Phe Leu Gly Met Ala Val Asn
        115                 120                 125

Thr Leu Cys Gly Glu Val Pro Leu Tyr Tyr Ile
    130                 135

<210> SEQ ID NO 9
<211> LENGTH: 108
<212> TYPE: PRT
<213> ORGANISM: Homo sapiens

<400> SEQUENCE: 9

Thr Thr Ala Thr Phe Ser Ile Gly Ser Thr Gly Leu Val Val Tyr Asp
1               5                   10                  15

Tyr Gln Gln Leu Leu Ile Ala Tyr Lys Pro Ala Pro Gly Thr Cys Cys
            20                  25                  30

Tyr Ile Met Lys Ile Ala Pro Glu Ser Ile Pro Ser Leu Glu Ala Leu
        35                  40                  45

Asn Arg Lys Val His Asn Phe Gln Met Glu Cys Ser Leu Gln Ala Lys
    50                  55                  60

Pro Ala Val Pro Thr Ser Lys Leu Gly Gln Ala Glu Gly Arg Asp Ala
65                  70                  75                  80

Gly Ser Ala Pro Ser Gly Gly Asp Pro Ala Phe Leu Gly Met Ala Val
                85                  90                  95

Asn Thr Leu Cys Gly Glu Val Pro Leu Tyr Tyr Ile
            100                 105

```
<210> SEQ ID NO 10
<211> LENGTH: 40
<212> TYPE: PRT
<213> ORGANISM: Homo sapiens

<400> SEQUENCE: 10

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 11
<211> LENGTH: 42
<212> TYPE: PRT
<213> ORGANISM: Homo sapiens

<400> SEQUENCE: 11

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 12
<211> LENGTH: 11
<212> TYPE: PRT
<213> ORGANISM: Artificial Sequence
<220> FEATURE:
<223> OTHER INFORMATION: V7 peptide

<400> SEQUENCE: 12

Lys Lys Val Val Val Val Val Val Val Lys Lys
1               5                   10

<210> SEQ ID NO 13
<211> LENGTH: 9
<212> TYPE: PRT
<213> ORGANISM: Artificial Sequence
<220> FEATURE:
<223> OTHER INFORMATION: V5 peptide

<400> SEQUENCE: 13

Lys Lys Val Val Val Val Val Lys Lys
1               5

<210> SEQ ID NO 14
<211> LENGTH: 11
<212> TYPE: PRT
<213> ORGANISM: Artificial Sequence
<220> FEATURE:
<223> OTHER INFORMATION: A7 peptide

<400> SEQUENCE: 14

Lys Lys Ala Ala Ala Ala Ala Ala Ala Lys Lys
1               5                   10
```